(12) United States Patent
Chu et al.

(10) Patent No.: US 7,465,542 B2
(45) Date of Patent: Dec. 16, 2008

(54) METHODS AND COMPOSITIONS FOR DETERMINING RISK OF TREATMENT TOXICITY

(75) Inventors: Gilbert Chu, Palo Alto, CA (US); Virginia G. Tusher, Belvedere, CA (US); Jean Tang, Stanford, CA (US); Kerri Elyse Rieger, Menlo Park, CA (US); Wan-Jen Hong, Palo Alto, CA (US); Robert Tibshirani, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 444 days.

(21) Appl. No.: 10/686,322

(22) Filed: Oct. 14, 2003

(65) Prior Publication Data

US 2004/0152109 A1   Aug. 5, 2004

Related U.S. Application Data

(60) Provisional application No. 60/419,016, filed on Oct. 15, 2002.

(51) Int. Cl.
*C12Q 1/68* (2006.01)
(52) U.S. Cl. .......................................... 435/6; 435/91.1
(58) Field of Classification Search ........................ None
See application file for complete search history.

(56) References Cited

U.S. PATENT DOCUMENTS

| | | | |
|---|---|---|---|
| 6,015,673 A * | 1/2000 | Gonzalez et al. | 435/6 |
| 6,251,362 B1 * | 6/2001 | Wahl et al. | 424/1.11 |
| 2003/0165954 A1 | 9/2003 | Katagiri et al. | |
| 2004/0018527 A1 | 1/2004 | Chang et al. | |

FOREIGN PATENT DOCUMENTS

WO    WO 01/84139    11/2001

OTHER PUBLICATIONS

Komarova et al. Oncogene vol. 17:1089-1096. 1998.*
Tibshirani et al. PNAS vol. 99:6567-6572. 2002.*
Barber et al., Relatinship Between in Vitro Chromosomal Readiosensitivity of Peripheral Blood Lymphocytes and the Expression of Normal Tissue Damage Following Radiotherapy for Breast Cancer, (2002), Radiother Oncol, 55:179-86.
Brock et al., In Vitro Radiosensitvity and Normal Tissue Damage, (2000), Radiother Oncol, 55:93-94.
Crompton et al., Altered Apoptotic Profiles in Irradiated Patients with Increased Toxicity, (1999), Int J Radiat Oncol Biol Phys, 45:707-714.
Johansen et al., Relationship Between the In Vitro Radiosensitivity of Skin Fibroblasts and the Expression of Subcutaneous Fibrosis, Telangiectasia, and Skin Erythema After Radiotherapy, (1996), Radiother Oncol, 40:101-9.
Peacock et al., Cellular Radiosensitvity and Complication Risk After Curative Radiotherapy, (2000), Radiother Oncol, 55:173-8.
Russell et al., Low Predictive Value of Intrinsic Fibroblast Radiosensitvity for Fibrosis Developemnt Following Radiotherapy for Breast Cancer, (1998), Int J Radiat Biol, 73:661-70.
Tibshirani et al., Diagnosis of Multiple Cancer Types by Shrunken Centroids of Gene Expression, (2002) Proc. Natl. Acad. Sci. 99:6567-6572.
Tusher et al., Significance Analysis of Microarrays Applied to the Ionizing Radiation Response, (2001), Proc. Natl. Acad. Sci., 98:5116-5121.

* cited by examiner

*Primary Examiner*—Gary Benzion
*Assistant Examiner*—Heather G Calamita
(74) *Attorney, Agent, or Firm*—Bozicevic, Field & Francis LLP; Pamela J. Sherwood

(57) ABSTRACT

Methods are provided for determining whether a patient treated with an anti-proliferative agent is susceptible to toxicity. In practicing the subject methods, an expression profile for the transcriptional response to a therapy is obtained from the patient and compared to a reference profile to determine whether the patient is susceptible to toxicity. In addition, reagents and kits thereof that find use in practicing the subject methods are provided.

12 Claims, 4 Drawing Sheets
(1 of 4 Drawing Sheet(s) Filed in Color)

METHODS AND COMPOSITIONS FOR DETERMINING RISK OF TREATMENT TOXICITY

Many anti-proliferative agents used to treat cancer; infections, etc. also have the potential to damage normal cells. Generally dosage levels are selected to preferentially affect the target, e.g. tumor cells, but some patients are particularly susceptible to toxicity, and can suffer undesirable side effects from such treatment.

For example, ionizing radiation (IR) is used to treat about 60% of cancer patients, by depositing energy that injures or destroys cells in the area being treated. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area.

Radiotherapy may be used in combination with additional agents. Radiosensitizers make the tumor cells more likely to be damaged, and radioprotectors protect normal tissues from the effects of radiation. Hyperthermia is also being studied for its effectiveness in sensitizing tissue to radiation.

Although most patients tolerate treatment, up to 10% of patients suffer from toxicity that can lead to significant morbidity. Non-genetic risk factors for radiation toxicity include concurrent treatment with radiosensitizing drugs and anatomical variations such as congenital malformations, post-surgical adhesions, fat content, and tissue oxygenation. Toxicity is also associated with diabetes and autoimmune diseases such as lupus. However, these causes cannot account for the vast majority of adverse radiation reactions.

In a small fraction of cases, radiation sensitivity can be attributed to known genetic mutations. Diseases of IR sensitivity include ataxia telangiectasia (AT), AT-like disorder, Nijmegan Breakage Syndrome, and radiosensitivity with severe combined immunodeficiency, but these autosomal recessive diseases are rare. Heterozygosity for mutations in ATM, the gene mutated in AT, may occur in 1% of individuals and has been reported to confer moderate sensitivity to IR in tissue culture. However, relatively few adverse radiation reactions are associated with ATM mutations.

Several attempts have been made to correlate radiation toxicity with cellular responses to IR ex vivo. Survival of cultured skin fibroblasts after IR correlated with acute radiation toxicity in some studies but not others (see Johansen et al. (1996) *Radiother Oncol* 40:101-9; Russell et al. (1998) *Int J Radiat Biol* 73:661-70; Peacock et al. (2000) *Radiother Oncol* 55:173-8. In another study, lymphocytes from cancer patients with radiation toxicity showed less IR-induced apoptosis than lymphocytes from control patients (Crompton et al. (1999) *Int J Radiat Oncol Biol Phys* 45:707-714). Peripheral blood lymphocytes from breast cancer patients with severe skin reactions showed an abnormal increase in chromosome aberrations when the cells were exposed to IR (Barber et al. (2000) *Radiother Oncol* 55:179-86). In these latter two studies, correlations between radiation toxicity and the ex vivo assay suggested the presence of an underlying genetic defect in some radiation sensitive patients. However, there was a large overlap between radiation sensitive patients and controls in these assays, limiting their clinical usefulness.

Thus, assays to predict radiation toxicity have yielded mixed results, and the vast majority of adverse reactions remain unexplained (Brock et al. (2000) *Radiother Oncol* 55:93-94).

To date, there is no effective way known to the inventors to predict whether or not a patient will be susceptible to toxicity following radiation therapy. A diagnostic protocol which could provide information as to whether a patient is or is not susceptible to toxicity would be desirable for a number of reasons, including avoidance of delays in alternative treatments, elimination of exposure to adverse effects and reduction of unnecessary expense. As such, there is interest in the development of a protocol that can accurately predict whether or not a patient is susceptible to toxicity from radiation therapy.

Relevant Literature

A method of analyzing the significance of changes observed in expression patterns in microarrays may be found in International Application WO 01/84139; and Tusher et al. (2001) *Proc. Natl. Acad. Sci. USA* 98:5116-5121. A method for analysis of shrunken centroids is described by Tibshirani et al. (2002) *Proc. Natl. Acad. Sci. USA* 99:6567-6572.

SUMMARY OF THE INVENTION

Methods are provided for predicting whether an individual subjected to anti-proliferative therapy, particularly therapy that results in DNA damage, e.g. radiation therapy will be susceptible to toxicity resulting from the therapy. The ability to predict susceptibility to toxicity allows optimization of treatment, and determination of whether on whether to proceed with a specific therapy, and how to optimize dose, choice of treatment, and the like. In another embodiment, methods are provided for determining whether an individual is susceptible to toxicity.

In practicing the methods, an expression profile is obtained from the subject cells in the absence and presence of the therapy, e.g. UV radiation, ionizing radiation, presence of a chemotherapeutic agent, etc. The expression profile is used to determine the difference between the exposed and non-exposed cells, and is compared to a reference profile. Reagents and kits thereof that find use in practicing the subject methods are provided.

In another embodiment of the invention, methods are provided for statistical analysis of data, such as expression profiles in response to a stimulus, e.g. treatment with drug, exposure to radiation, exposure to specific antigenic stimulus, and the like; post-translational responses, basal expression levels; etc. to determine whether a pattern of expression or response will be predictive of a phenotype of interest. The statistical analyses usually utilize a heterogeneity-associated transformation, and nearest shrunken centroids analysis to provide a set of predictive genes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4. Hierarchical clustering of genes that predict radiation toxicity. Data are shown for the 52 top-ranked predictive genes identified by HAT/NSC. The dendrogram above the heat map shows clustering of the 57 subjects. Shaded boxes under the dendrogram indicate the classes of subjects. The dendrogram to the left of the heat map shows clustering of the 52 genes represented by 55 probe sets. The colored boxes to the right of the heat map indicate biological function of the genes. An asterisk next to the gene description indicates UV-response data. All other data are IR-response data. Accession number, symbol, and rank in our prediction protocol are listed for each gene. Three predictive genes are listed twice, since two different probe sets (specified in parentheses) for the same gene were found to be predictive. In each case, probe sets for the same gene were closely clustered. Because centered Pearson correlation was used for clustering, genes with changes in expression that varied in the same way across samples were clustered together, independently of average changes in expression. For example, CALM1 and BASP1, two genes at the top of the heat map, were clustered together even though CALM1 was generally repressed and BASP1 was generally induced. To provide a scale for the IR-response data, the upper right panel shows the distribution of average IR responses for all 12,625 probe sets in samples from 15 subjects without cancer. The distribution of UV responses was similar.

DETAILED DESCRIPTION OF THE EMBODIMENTS

Figure 1:
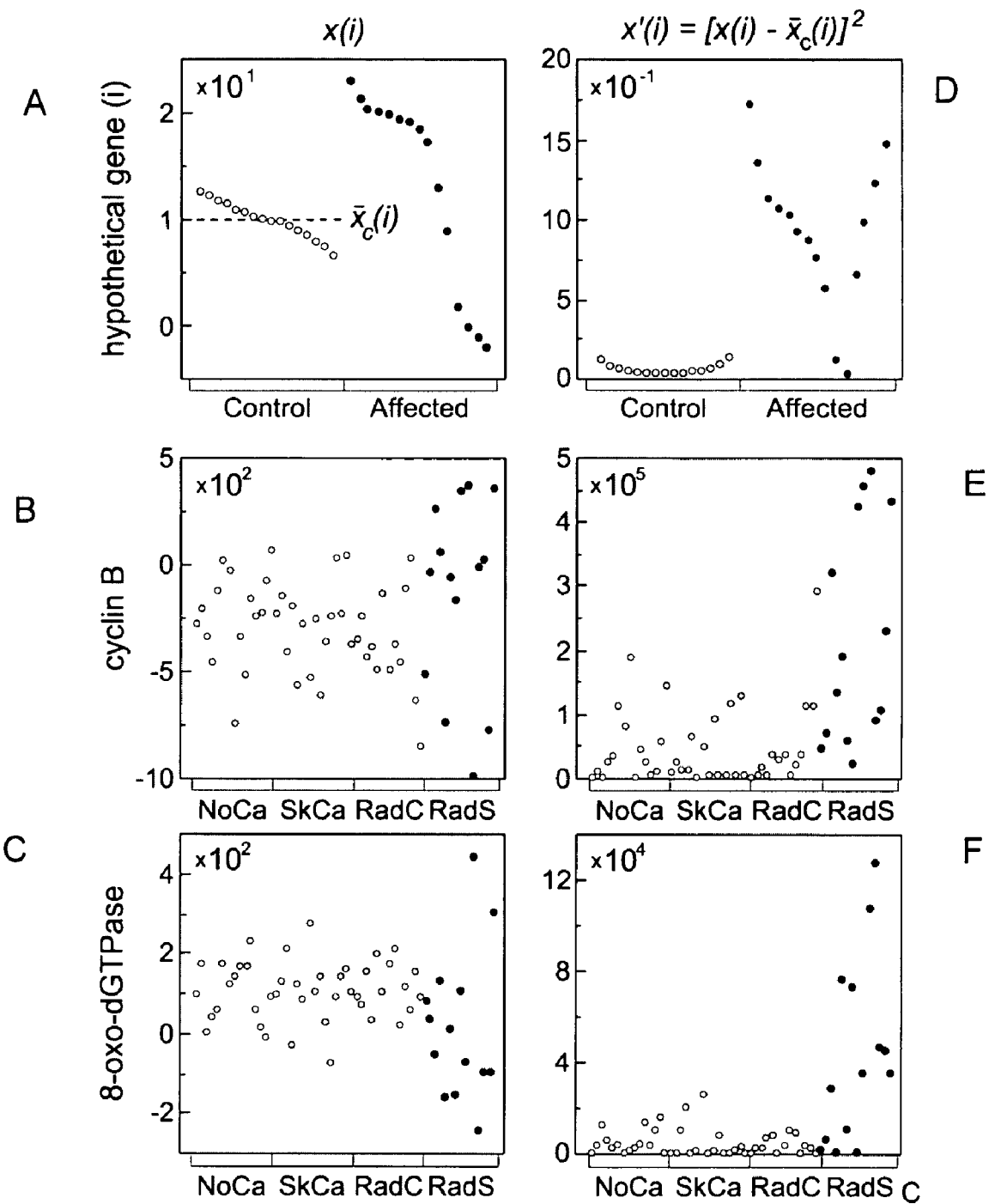
FIGS. 1A-1F. Effect of heterogeneity-associated transformation (HAT) on gene expression data. The left panels show changes in gene expression after DNA damage, x(i), for gene i. The dashed line marks $\bar{x}_c(i)$, the average x(i) among the controls. The right panels show data after HAT, which was more effective in separating the radiation sensitive patients from controls. The upper panels show a hypothetical gene with transcriptional responses that were blunted in some patients and enhanced in others. The middle and lower panels show actual data for two predictive genes, cyclin B and 8-oxo-dGTPase. Patient samples were arranged by predicted probability for radiation toxicity (see FIG. 3).

The subject invention provides a method of determining whether a patient is susceptible to toxicity resulting from anti-proliferative therapy, where the method includes (a) obtaining a transcriptional response profile for a sample from said subject in the absence or presence of said therapy; and (b) comparing said obtained profile to a reference expression profile to determine whether said subject is susceptible to said toxicity. In certain embodiments, the expression profile is for at least about 10, usually at least about 25, and may be at least 50, at least about 100, or more of said genes listed in Table 3. In certain embodiments, the expression profile is determined using a microarray. In other embodiments the expression profile is determined by quantitative PCR or other quantitative methods for measuring mRNA.

The subject invention also provides a reference expression profile for a response phenotype that is one of: (a) susceptible to toxicity; or (b) non-susceptible to toxicity; wherein said expression profile is recorded on a computer readable medium.

For quantitative PCR analysis, the subject invention provides a collection of gene specific primers, said collection comprising: gene specific primers specific for at least about 10, usually at least about 20 of the genes of Table 3, where in certain embodiments said collection comprises at least 50 gene specific primers, at least 100, or more. The subject invention also provides an array of probe nucleic acids immobilized on a solid support, said array comprising: a plurality of probe nucleic acid compositions, wherein each probe nucleic acid composition is specific for a gene whose expression profile is indicative of toxicity susceptibility phenotype, wherein at least 10 of said probe nucleic acid compositions correspond to genes listed in Table 3, where in certain embodiments said array further comprises at least one control nucleic acid composition.

The subject invention also provides a kit for use in determining the susceptibility phenotype of a source of a nucleic acid sample, said kit comprising: at least one of: (a) an array as described above; or (b) a collection of gene specific primers as described above. The kit may further comprise a software package for data analysis of expression profiles.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

As summarized above, the subject invention is directed to methods of determining whether a subject is susceptible to unacceptable toxicity in response to therapeutic procedures, as well as reagents and kits for use in practicing the subject methods. The methods may also determine whether a particular cancer cell is susceptible to killing by a therapy of interest, where the differential between the target cell, e.g. a cancer cell, and the normal cell, is useful in making a determination of suitable treatment.

Methods are also provided for optimizing therapy, by determining the susceptibility of a patient to toxicity induced by one or more therapies, and based on that information, selecting the appropriate therapy, dose, treatment modality, e.g. angle and screening of radiation, etc. which optimizes the differential between delivery of an anti-proliferative treatment to the undesirable target cells, while minimizing undesirable toxicity. In one embodiment of the invention, the patient sample is exposed to two or more candidate therapies or combinations of therapies, e.g. exposure to various chemotherapeutic agents. Optionally, both a normal cell sample and a tumor cell sample are tested, in order to determine the differential effect of the treatment on normal and tumor cells. The treatment is optimized by selection for a treatment that avoids treatment that has a high probability of causing undesirable toxicity, while providing for effective anti-proliferative activity.

In further describing the invention, the subject methods are described first, followed by a review of the reagents and kits for use in practicing the subject methods.

Anti-Proliferative Agents and Treatments

Anti-proliferative therapy is used therapeutically to eliminate tumor cells and other undesirable cells in a host, and includes the use of therapies such as delivery of ionizing radiation, and administration of chemotherapeutic agents. Chemotherapeutic agents of particular interest induce DNA damage, and more particularly agents of interest induce double stranded breaks in DNA, for example the topoisomerase inhibitors anthracyclines, including the compounds daunorubicin, adriamycin (doxorubicin), epirubicin, idarubicin, anamycin, MEN 10755, and the like. Other topoisomerase inhibitors include the podophyllotoxin analogues etoposide and teniposide, and the anthracenediones, mitoxantrone and amsacrine.

In one aspect of the invention, the anti-proliferative agent interferes with microtubule assembly, e.g. the family of vinca alkaloids. Examples of vinca alkaloids include vinblastine, vincristine; vinorelbine (NAVELBINE); vindesine; vindoline; vincamine; etc.

In another embodiment of the invention, the anti-proliferative agent is a DNA-damaging agent, such as nucleotide analogs, alkylating agents, etc. Alkylating agents include nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc.

Nucleotide analogs include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc.

Other chemotherapeutic agents of interest include metal complexes, e.g. cisplatin (cis-DDP), carboplatin, oxaliplatin, etc.; ureas, e.g. hydroxyurea; and hydrazines, e.g. N-methylhydrazine.

Toxicity

The use of anti-proliferative agents and treatments in therapy, e.g. in cancer therapy, depends on a differential between the effect on undesirable cancer cells and normal cells. Certain patients are less tolerant of treatment, and suffer unacceptable toxicity in normal tissues. It will be understood by those of skill in the art that some level of damage may occur in all subjects. It will also be understood that the toxic effects may be found on various tissues, i.e. skin, central nervous system, gut, etc. depending on the specific angle and dose of therapeutic radiation, compound that is delivered, etc. Criteria for grading toxic effects are known in the art, and are reproduced herein for convenience. The methods of the present invention are useful in differentiating between patients susceptible to unacceptable toxicity, i.e. having a grade of 2, 3, 4 or 5 in any tissue; and patients susceptible to acceptable toxicity of only grade 0 or 1.

The following tables provide conventional criteria for grading radiation toxicity. Other toxicities associated with other agents are known in the relevant clinical arts, and will be readily obtained by one of skill in the art. Toxicity may occur within less than about 90 days following exposure, herein termed early toxicity, or may occur after greater than about 90 days, herein termed late toxicity.

TABLE 1

| | [0] | [1] | [2] | [3] | [4] |
|---|---|---|---|---|---|
| Early Toxicity | | | | | |
| Skin | No change over baseline | Follicular, faint or dull erythema/epilation/dry desquamation/decreased sweating | Tender or bright erythema, patchy moist desquamation/ moderate edema | Confluent, moist desquamatiom other than skin folds, pitting edema | Ulceration, hemorrhage, necrosis |
| Mucous Membrane | No change over baseline | Injection/may experience mild pain not requiring analgesic | Patchy mucositis which may produce an inflammatory serosanguinitis discharge/may | Confluent fibrinous mucositis/may include severe pain requiring narcotic | Ulceration, hemorrhage or necrosis |

TABLE 1-continued

| | | | Early Toxicity | | |
|---|---|---|---|---|---|
| | [0] | [1] | [2] | [3] | [4] |
| Eye | No change | Mild conjunctivitis with or without scleral injection/ increased tearing | experience moderate pain requiring analgesia Moderate conjunctivitis with or without keratitis requiring steroids &/or antibiotics/dry eye requiring artificial tears/ iritis with photophobia | Severe keratitis with corneal ulceration/ objective decrease in visual acuity or in visual fields/acute glaucoma/ panopthalmitis | Loss of vision (unilateral or bilateral) |
| Ear | No change over baseline | Mild external otitis with erythema, pruritis, secondary to dry desquamation not requiring medication. Audiogram unchanged from baseline | Moderate external otitis requiring topical medication/serious otitis medius/ hypoacusis on testing only | Severe external otitis with discharge or moist desquamation/ symptomatic hypoacusis/tinnitus, not drug related | Deafness |
| Salivary Gland | No change over baseline | Mild mouth dryness/ slightly thickened saliva/ may have slightly altered taste such as metallic taste | Moderate to complete dryness/thick, sticky saliva/markedly altered taste | | Acute salivary gland necrosis |
| Pharynx & Esophagus | No change over baseline | Mild dysphagia or odynophagia/may require topical anesthetic or non-narcotic analgesics/may require soft diet | Moderate dysphagia or odynophagia/may require narcotic analgesics/may require puree or liquid diet | Severe dysphagia or odynophagia with dehydration or weight loss (>15% from pretreatment baseline) requiring N-G feeding tube, I.V. fluids or hyperalimentation | Complete obstruction, ulceration, perforation, fistula |
| Larynx | No change over baseline | Mild or intermittent hoarseness/cough not requiring antitussive/ erythema of mucosa | Persistent hoarseness but able to vocalize/ referred ear pain, sore throat, patchy fibrinous exudate or mild arytenoid edema not requiring narcotic/ cough requiring antitussive | Whispered speech, throat pain or referred ear pain requiring narcotic/ confluent fibrinous exudate, marked arytenoid edema | Marked dyspnea, stridor or hemoptysis with tracheostomy or intubation necessary |
| Upper G.I. | No change | Anorexia with <=5% weight loss from pretreatment baseline/ nausea not requiring antiemetics/abdominal discomfort not requiring parasympatholytic drugs or analgesics | Anorexia with <=15% weight loss from pretreatment baseline/nausea &/or vomiting requiring antiemetics/abdominal pain requiring analgesics | Anorexia with >15% weight loss from pretreatment baseline or requiring N-G tube or parenteral support. Nausea &/or vomiting requiring tube or parenteral support/abdominal pain, severe despite medication/hematemesis or melena/abdominal distention (flat plate radiograph demonstrates distended bowel loops | Ileus, subacute or acute obstruction, performation, GI bleeding requiring transfusion/abdominal pain requiring tube decompression or bowel diversion |
| Lower G.I. Including Pelvis | No change | Increased frequency or change in quality of bowel habits not requiring medication/rectal discomfort not requiring analgesics | Diarrhea requiring parasympatholytic drugs (e.g., Lomotil)/mucous discharge not necessitating sanitary pads/rectal or abdominal pain requiring analgesics | Diarrhea requiring parenteral support/ severe mucous or blood discharge necessitating sanitary pags/abdominal distention (flat plate radiograph demonstrates distended bowel loops) | Acute or subacute obstruction, fistula or perforation; GI bleeding requiring transfusion; abdominal pain or tenesmus requiring tube decompression or bowel diversion |
| Lung | No change | Mild symptoms of dry cough or dyspnea on exertion | Persistent cough requiring narcotic, antitussive agents/ dyspnea with minimal effort but not at rest | Severe cough unresponsive to narcotic antitussive agent or dyspnea at rest/clinical or radiologic evidence of acute pneumonitis/ intermittent oxygen or steroids may be required | Severe respiratory insufficiency/ continuous oxygen or assisted ventilation |
| Genitourinary | No change | Frequency of urination or nocturia twice pretreatment habit/ dysuria, urgency not requiring medication | Frequency of urination or nocturia which is less frequent than every hour. Dysuria, urgency, bladder spasm requiring local anesthetic (e.g., | Frequency with urgency and nocturia hourly or more frequently/dysuria, pelvis pain or bladder spasm requiring regular, frequent narcotic/gross | Hematuria requiring transfusion/acute bladder obstruction not secondary to clot passage, ulceration or necrosis |

TABLE 1-continued

Early Toxicity

| | [0] | [1] | [2] | [3] | [4] |
|---|---|---|---|---|---|
| | | | Pyridium) | hematuria with/without clot passage | |
| Heart | No change over baseline | Asymptomatic but objective evidence of EKG changes or pericardial abnormalities without evidence of other heart disease | Symptomatic with EKG changes and radiologic findings of congestive heart failure or pericardial disease/no specific treatment required | Congestive heart failure, angina pectoris, pericardial disease responding to therapy | Congestive heart failure, angina pectoris, pericardial disease, arrhythmias not responsive to non-surgical measures |
| Cns | No change | Fully functional status (i.e., able to work) with minor neurologic findings, no medication needed | Neurologic findings present sufficient to require home case/ nursing assistance may be required/ medications including steroids/anti-seizure agents may be required | Neurologic findings requiring hospitalization for initial management | Serious neurologic impairment which includes paralysis, coma or seizures > 3 per week despite medication/hospitalization required |
| Hematologic Wbc (X 1000) | >=4.0 | 3.0-<4.0 | 2.0-<3.0 | 1.0-<2.0 | <1.0 |
| Platelets (X 1000) | >100 | 75-<100 | 50-<=75 | 25-<50 | <25 or spontaneous bleeding |
| Neutrophils | >=1.9 | 1.5-<1.9 | 1.0-<1.5 | 0.5-<=1.0 | <=0.5 or sepsis |
| Hemoglobin (Gm %) | >11 | 11-9.5 | <9.5-7.5 | <7.5-5.0 | — |
| Hematocrit (%) | >=32 | 28-<32 | <=28 | Packed cell transfusion required | — |

TABLE 2

Late Toxicity

| Organ Tissue | 0 | Grade 1 | Grade 2 | Grade 3 | Grade 4 |
|---|---|---|---|---|---|
| Skin | None | Slight atrophy Pigmentation change Some hair loss | Patch atrophy; Moderate telangiectasia; Total hair loss | Marked atrophy; Gross telangiectasia | Ulceration |
| Subcutaneous Tissue | None | Slight induration (fibrosia) and loss of subcutaneous fat | Moderate fibrosis but asymptomatic Slight field contracture <10% linear reduction | Severe induration and loss of subcutaneous tissue Field contracture >10% linear measurement | Necrosis |
| Mucous Membrane | None | Slight atrophy and dryness | Moderate atrophy and telangiectasia Little mucous | Marked atrophy with complete dryness Severe telangiectasia | Ulceration |
| Salivary Glands | None | Slight dryness of mouth Good response on stimulation | Moderate dryness of mouth Poor response on stimulation | Complete dryness of mouth No response on stimulation | Fibrosis |
| Spinal Cord | None | Mild L'Hermitte's syndrome | Severe L'Hermitte's syndrome | Objective neurological findings at or below cord level treated | Mono, para quadraplegia |
| Brain | None | Mild headache Slight lethargy | Moderate headache Great lethargy | Severe headaches Severe CNS dysfunction (partial loss of power or dyskinesia) | Seizures or paralysis Coma |
| Eye | None | Asymptomatic cataract Minor corneal ulceration or keratitis | Symptomatic cataract Moderate corneal ulceration Minor retinopathy or glaucoma | Severe keratitis Severe retinopathy or detachment Severe glaucoma | Panopthalmitis/ Blindness |
| Larynx | None | Hoarseness Slight arytenoid edema | Moderate arytenoid edema Chondritis | Severe edema Severe chondritis | Necrosis |
| Lung | None | Asymptomatic or mild symptoms (dry cough) Slight radiographic appearances | Moderate symptomatic fibrosis or pneumonitis (severe cough) Low grade fever Patchy radiographic appearances | Severe symptomatic fibrosis or pneumonitis Dense radiographic changes | Severe respiratory insufficiency/ Continuous O2/ Assisted ventilation |
| Heart | None | Asymptomatic or mild symptoms Transient T wave inversion & ST changes Sinus tachycardia >110 (at rest) | Moderate angina on effort Mild pericarditis Normal heart size Persistent abnormal T wave and ST changes Low ORS | Severe angina Pericardial effusion Constrictive pericarditis Moderate heart failure Cardiac enlargement EKG abnormalities | Tamponade/Severe heart failure/Severe constrictive pericarditis |

TABLE 2-continued

Late Toxicity

| Organ Tissue | 0 | Grade 1 | Grade 2 | Grade 3 | Grade 4 |
|---|---|---|---|---|---|
| Esophagus | None | Mild fibrosis Slight difficulty in swallowing solids No pain on swallowing | Unable to take solid food normally Swallowing semi-solid food Dilatation may be indicated | Severe fibrosis Able to swallow only liquids May have pain on swallowing Dilation required | Necrosis/Perforation Fistula |
| Small/Large Intestine | None | Mild diarrhea Mild cramping Bowel movement 5 times daily Slight rectal discharge or bleeding | Moderate diarrhea and colic Bowel movement >5 times daily Excessive rectal mucus or intermittent bleeding | Obstruction or bleeding requiring surgery | Necrosis/ PerforationFistula |
| Liver | None | Mild lassitude Nausea, dyspepsia Slightly abnormal liver function | Moderate symptoms Some abnormal liver function tests Serum albumin normal | Disabling hepatitic insufficiency Liver function tests grossly abnormal Low albumin Edema or ascites | Necrosis/Hepatic coma or encephalopathy |
| Kidney | None | Transient albuminuria No hypertension Mild impairment of renal function Urea 25-35 mg % Creatinine 1.5-2.0 mg % Creatinine clearance >75% | Persistent moderate albuminuria (2+)Mild hypertension No related anemia Moderate impairment of renal function Urea > 36-60 mg % Creatinine clearance (50-74%) | Severe albuminuria Severe hypertension Persistent anemia (<10 g %) Severe renal failure Urea >60 mg % Creatinine >4.0 mg % Creatinine clearance <50% | Malignant hypertension Uremic coma/Urea >100% |
| Bladder | None | Slight epithelial atrophy Minor telangiectasia (microscopic hematuria) | Moderate frequency Generalized telangiectasia Intermittent macroscopic hematuria | Severe frequency and dysuria Severe generalized telangiectasia (often with petechiae) Frequent hematuria Reduction in bladder capacity (<150 cc) | Necrosis/Contracted bladder (capacity <100 cc) Severe hemorrhagic cystitis |
| Bone | None | Asymptomatic No growth retardation Reduced bone density | Moderate pain or tenderness Growth retardation Irregular bone sclerosis | Severe pain or tenderness Complete arrest of bone growth Dense bone sclerosis | Necrosis/ Spontaneous fracture |
| Joint | None | Mild joint stiffness Slight limitation of movement | Moderate stiffness Intermittent or moderate joint pain Moderate limitation of movement | Severe joint stiffness Pain with severe limitation of movement | Necrosis/Complete fixation |

Any toxicity that causes death is graded 5.

Methods of Determining Susceptibility

The subject invention provides methods of predicting whether a patient or subject exposed to anti-proliferative therapy, particularly therapy resulting in double stranded DNA damage, e.g. ionizing radiation, including X-rays, gamma radiation, etc.; treatment with topoisomerase inhibitors as described above, and the like; will be susceptible to toxicity. In practicing the subject methods, a subject or patient sample, e.g., cells or collections thereof, e.g., tissues, is assayed to determine whether the host from which the assayed sample was obtained is susceptible to toxicity. Cells of interest particularly include dividing cells, e.g. leukocytes, fibroblasts, epithelial cells, etc. Cell samples are collected by any convenient method, as known in the art. Additionally, tumor cells may be collected and tested to determine the relative effectiveness of a therapy in causing differential death between normal and diseased cells.

To test for radiation-induced toxicity, the cell sample is exposed to radiation, including at least ionizing radiation, and preferably one cell sample is exposed to ionizing radiation and a second cell sample is exposed to ultraviolet radiation. A suitable dose of ionizing radiation may range from at least about 2 Gy to not more than about 10 Gy, usually about 5 Gy. The sample may be collected from at least about 2 and not more than about 24 hours following ionizing radiation, usually around about 4 hours. A suitable dose of ultraviolet radiation may range from at least about 5 J/m$^2$ to not more than about 50 J/m$^2$, usually about 10 J/m$^2$. The sample may be collected from at least about 4 and not more than about 72 hours following ultraviolet radiation, usually around about 4 hours. The radiation exposed cell sample is assayed to obtain an expression profile for a set of genes, typically including at least about 10 top ranked genes set forth in Table 3, usually including at least about 25 top ranked genes, and may include at least about 50 top ranked genes; 100 top-ranked genes, or more, up to the complete set of predictive genes.

To test for toxicity resulting from exposure to chemotherapeutic agents, the cell sample may be exposed to radiation, as described above, or may be exposed to the therapeutic agent of interest, or to an agent having a similar profile of activity. Typically a cell sample will be compared to a control sample that has not been exposed to the therapy. The dose and time period for obtaining samples following exposure will vary with the specific agent that is selected. As is known in the art, a titration of dose may be used to determine the appropriate range for testing. Generally, samples from the cells will be obtained after at least about 4 hours and not more than about 5 days following exposure.

The term expression profile is used broadly to include a genomic expression profile, e.g., an expression profile of mRNAs, or a proteomic expression profile, e.g., an expression profile of one or more different proteins. Profiles may be generated by any convenient means for determining differential gene expression between two samples, e.g. quantitative hybridization of mRNA, labeled mRNA, amplified mRNA, cRNA, etc., quantitative PCR, ELISA for protein quantitation, and the like.

Genes/proteins of interest are genes/proteins that are found to be predictive of susceptibility to toxicity include, but are not limited to, the genes/proteins provided in Table 3, below

TABLE 3

| Rank | Accession | Symbol | Name | IR or UV response |
|---|---|---|---|---|
| 1 | M25753 | HUMCYCB | Cyclin B | UV |
| 2 | AI436567 | ATP5D | ATP synthase, H+ transporting, mitochondrial F1 complex, delta subunit | IR |
| 3 | X54942 | CKS2 | CDC28 protein kinase 2 | UV |
| 4 | AB011126 | FBP17 | formin-binding protein 17 | IR |
| 5 | U14971 | RPS9 | ribosomal protein S9 | IR |
| 6 | AL022318 | MDS019 | phorbolin-like protein MDS019 | IR |
| 7 | L08096 | TNFSF7 | tumor necrosis factor (ligand) superfamily, member 7 | IR |
| 8 | AL080113 | | RNA helicase | IR |
| 9 | AI126004 | SAS10 | disrupter of silencing 10 | IR |
| 10 | Z23090 | HSPB1 | heat shock 27kD protein 1 | IR |
| 11 | D21090 | RAD23B | RAD23 homolog B | IR |
| 12 | U35451 | CBX1 | chromobox homolog 1 (HP1 beta) | IR |
| 13 | AA890010 | | | IR |
| 14 | M65028 | HNRPAB | heterogeneous nuclear ribonucleoprotein A/B | IR |
| 15 | D26600 | PSMB4 | proteasome (prosome, macropain) subunit, beta type, 4 | IR |
| 16 | AF072810 | BAZ1B | bromodomain adjacent to zinc finger domain, 1B | IR |
| 17 | U49869 | | ubiquitin | IR |
| 18 | D16581 | NUDT1 | nudix (nucleoside diphosphate linked moiety X)-type motif 1 | IR |
| 19 | AA121509 | LOC51690 | U6 snRNA-associated Sm-like protein LSm7 | IR |
| 20 | X81625 | ETF1 | eukaryotic translation termination factor 1 | IR |
| 21 | Z48501 | PABPC1 | poly(A)-binding protein, cytoplasmic 1 | IR |
| 22 | AA121509 | LOC51690 | U6 snRNA-associated Sm-like protein LSm7 | IR |
| 23 | U12022 | CALM1 | calmodulin | UV |
| 24 | U52682 | IRF4 | interferon regulatory factor 4 | IR |
| 25 | J03592 | SLC25A6 | solute carrier family 25 (mitochondrial carrier; adenine nucleotide translocator), member 6 | IR |
| 26 | J03161 | SRF | serum response factor (c-fos serum response element-binding transcription factor) | IR |
| 27 | Z11692 | EEF2 | eukaryotic translation elongation factor 2 | IR |
| 28 | X83218 | ATP5O | ATP synthase, H+ transporting, mitochondrial F1 complex, O subunit (oligomycin sensitivity conferring protein) | IR |
| 29 | X51688 | CCNA2 | cyclin A2 | UV |
| 30 | U11861 | G10 | maternal G10 transcript | IR |
| 31 | D44466 | PSMD1 | proteasome (prosome, macropain) 26S subunit, non-ATPase, 1 | IR |
| 32 | AB019392 | M9 | muscle specific gene | IR |
| 33 | AI991040 | DRAP1 | DR1-associated protein 1 (negative cofactor 2 alpha) | IR |
| 34 | X70944 | SFPQ | splicing factor proline/glutamine rich (polypyrimidine tract-binding protein-associated) | UV |
| 35 | M25753 | | Cyclin B1 | UV |
| 36 | X15414 | AKR1B1 | aldo-keto reductase family 1, member B1 (aldose reductase) | IR |
| 37 | U12779 | MAPKAPK2 | mitogen-activated protein kinase-activated protein kinase 2 | IR |
| 38 | Z49254 | MRPL23 | mitochondrial ribosomal protein L23 | IR |
| 39 | J02683 | SLC25A5 | solute carrier family 25 (mitochondrial carrier; adenine nucleotide translocator), member 5 | UV |
| 40 | S87759 | PPM1A | protein phosphatase 1A (formerly 2C), magnesium-dependent, alpha isoform | IR |
| 41 | D32050 | AARS | alanyl-tRNA synthetase | UV |
| 42 | X06617 | RPS11 | ribosomal protein S11 | IR |
| 43 | AF023676 | TM7SF2 | transmembrane 7 superfamily member 2 | IR |
| 44 | AB002368 | KIAA0370 | KIAA0370 protein | IR |
| 45 | AB029038 | KIAA1115 | KIAA1115 protein | IR |
| 46 | D45248 | PSME2 | proteasome (prosome, macropain) activator subunit 2 (PA28 beta) | IR |
| 47 | D13641 | KIAA0016 | translocase of outer mitochondrial membrane 20 (yeast) homolog | IR |
| 48 | M58378 | | | IR |
| 49 | Y18418 | RUVBL1 | RuvB (E coli homolog)-like 1 | UV |
| 50 | L20298 | CBFB | core-binding factor, beta subunit | IR |
| 51 | L24804 | P23 | unactive progesterone receptor, 23kD | UV |
| 52 | AF039656 | BASP1 | brain abundant, membrane attached signal protein 1 | UV |
| 53 | AL022721 | PPARD | peroxisome proliferative activated receptor, delta | IR |
| 54 | U48734 | ACTN4 | actinin, alpha 4 | IR |
| 55 | Z49148 | RPL29 | ribosomal protein L29 | IR |
| 56 | U68063 | SFRS10 | splicing factor, arginine/serine-rich (transformer homolog) 10 | UV |

TABLE 3-continued

| Rank | Accession | Symbol | Name | IR or UV response |
|---|---|---|---|---|
| 57 | AJ005259 | EDF1 | endothelial differentiation-related factor 1 | IR |
| 58 | U05340 | CDC20 | CDC20 (cell division cycle 20 homolog) | UV |
| 59 | M72709 | SFRS1 | splicing factor, arginine/serine-rich 1 (splicing factor 2, alternate splicing factor) | UV |
| 60 | U15932 | DUSP5 | dual specificity phosphatase 5 | UV |
| 61 | M61764 | TUBG1 | tubulin, gamma 1 | UV |
| 62 | AI857469 | TCEB2 | transcription elongation factor B (SIII), polypeptide 2 (18kD, elongin B) | IR |
| 63 | AL022318 | MDS019 | phorbolin-like protein MDS019 | UV |
| 64 | AB011114 | KIAA0542 | KIAA0542 gene product | IR |
| 65 | X71874 | | | IR |
| 66 | L07956 | GBE1 | glucan (1,4-alpha-), branching enzyme 1 (glycogen branching enzyme | IR |
| 67 | AF053356 | | | IR |
| 68 | L31584 | EBI 1 | G protein-coupled receptor | IR |
| 69 | X78992 | ZFP36L2 | zinc finger protein 36, C3H type-like 2 | IR |
| 70 | M81757 | RPS19 | ribosomal protein S19 | IR |
| 71 | AL031670 | | | IR |
| 72 | W07033 | GMFG | glia maturation factor, gamma | IR |
| 73 | Z98046 | | | IR |
| 74 | U47101 | NIFU | nitrogen fixation cluster-like | IR |
| 75 | L11566 | RPL18 | ribosomal protein L18 | IR |
| 76 | U75686 | | polyadenylate binding protein | UV |
| 77 | M83664 | HLA-DPB1 | major histocompatibility complex, class II, DP beta 1 | UV |
| 78 | AL050021 | | | IR |
| 79 | M93425 | PTPN12 | protein tyrosine phosphatase, non-receptor type 12 | IR |
| 80 | U94905 | DGKZ | diacylglycerol kinase, zeta (104kD) | UV |
| 81 | Y08614 | XPO1 | exportin 1 (CRM1, yeast, homolog) | IR |
| 82 | AI540957 | QP-C | low molecular mass ubiquinone-binding protein (9.5kD) | IR |
| 83 | Z26876 | RPL38 | ribosomal protein L38 | IR |
| 84 | U28386 | KPNA2 | karyopherin alpha 2 (RAG cohort 1, importin alpha 1) | IR |
| 85 | X65550 | MKI67 | antigen identified by monoclonal antibody Ki-67 | UV |
| 86 | S72008 | CDC10 | CDC10 (cell division cycle 10 homolog) | IR |
| 87 | U03398 | TNFSF9 | tumor necrosis factor (ligand) superfamily, member 9 | IR |
| 88 | AF049910 | TACC1 | transforming, acidic coiled-coil containing protein 1 | IR |
| 89 | D42043 | KIAA0084 | KIAA0084 protein | IR |
| 90 | AB002313 | PLXNB2 | plexin B2 | UV |
| 91 | X97074 | AP2S1 | adaptor-related protein complex 2, sigma 1 subunit | IR |
| 92 | AB002323 | DNCH1 | dynein, cytoplasmic, heavy polypeptide 1 | UV |
| 93 | AF047185 | NDUFA2 | NADH dehydrogenase (ubiquinone) 1 alpha subcomplex, 2 (8kD, B8) | IR |
| 94 | AI819948 | MEL | mel transforming oncogene (derived from cell line NK14)-RAB8 homolog | UV |
| 95 | U14970 | RPS5 | ribosomal protein S5 | IR |
| 96 | AI375913 | TOP2A | topoisomerase (DNA) II alpha (170kD) | IR |
| 97 | AI541050 | NDUFB8 | NADH dehydrogenase (ubiquinone) 1 beta subcomplex, 8 (19kD, ASHI) | IR |
| 98 | D86979 | KIAA0226 | KIAA0226 gene product | IR |
| 99 | Z36714 | CCNF | cyclin F | IR |
| 100 | M30938 | XRCC5 | X-ray repair complementing defective repair (double-strand-break rejoining; Ku autoantigen) | UV |
| 101 | J03191 | PFN1 | profilin 1 | UV |
| 102 | X65923 | FAU | ribosomal protein S30 | IR |
| 103 | AF035555 | HADH2 | hydroxyacyl-Coenzyme A dehydrogenase, type II | IR |
| 104 | X72889 | SMARCA2 | SWI/SNF related, matrix associated, actin dependent regulator of chromatin, subfamily a, member 2 | IR |
| 105 | L22473 | BAX | BCL2-associated X protein | UV |
| 106 | U09813 | ATP5G3 | ATP synthase, H+ transporting, mitochondrial F0 complex, subunit c (subunit 9) isoform 3 | IR |
| 107 | Y00371 | hsc70 | 71kd heat shock cognate protein | IR |
| 108 | U94855 | EIF3S5 | eukaryotic translation initiation factor 3, subunit 5 (epsilon, 47kD) | IR |
| 109 | AA808961 | PSMB9 | proteasome (prosome, macropain) subunit, beta type, 9 (large multifunctional protease 2) | IR |
| 110 | AF053356 | | | UV |
| 111 | AF005392 | | | UV |
| 112 | L01124 | RPS13 | ribosomal protein S13 | IR |
| 113 | X00457 | HLA-DPA1 | major histocompatibility complex, class II, DP alpha 1 | UV |
| 114 | AI800499 | AIM1 | absent in melanoma 1 | IR |
| 115 | Y08110 | SORL1 | sortilin-related receptor, L(DLR class) A repeats-containing | UV |
| 116 | U12472 | GSTP1 | glutathione S-transferase pi | IR |
| 117 | X78992 | ZFP36L2 | zinc finger protein 36, C3H type-like 2 | UV |
| 118 | X91257 | SARS | seryl-tRNA synthetase | IR |
| 119 | M81757 | RPS19 | ribosomal protein S19 | UV |

TABLE 3-continued

| Rank | Accession | Symbol | Name | IR or UV response |
|---|---|---|---|---|
| 120 | AF037448 | NSAP1 | NS1-associated protein 1 | IR |
| 121 | AL022394 | | | UV |
| 122 | U67156 | MAP3K5 | mitogen-activated protein kinase kinase kinase 5 | IR |
| 123 | AF087135 | ATP5H | ATP synthase, H+ transporting, mitochondrial F0 complex, subunit d | IR |
| 124 | N24355 | POLR2L | polymerase (RNA) II (DNA directed) polypeptide L (7.6kD) | IR |
| 125 | D78134 | CIRBP | cold inducible RNA-binding protein | IR |
| 126 | X81625 | ETF1 | eukaryotic translation termination factor 1 | UV |
| 127 | X13710 | GPX1 | glutathione peroxidase 1 | IR |
| 128 | U18321 | DAP3 | death associated protein 3 | IR |
| 129 | AF072810 | BAZ1B | bromodomain adjacent to zinc finger domain, 1B | UV |
| 130 | X82240 | TCL1A | T-cell leukemia/lymphoma 1A | IR |
| 131 | D26598 | PSMB3 | proteasome (prosome, macropain) subunit, beta type, 3 | IR |
| 132 | X97548 | TRIM28 | tripartite motif-containing 28 | UV |
| 133 | D49738 | CKAP1 | cytoskeleton-associated protein 1 | IR |
| 134 | D87078 | PUM2 | pumilio homolog 2 | IR |
| 135 | U49278 | UBE2V1 | ubiquitin-conjugating enzyme E2 variant 1 | UV |
| 136 | U18300 | DDB2 | damage-specific DNA binding protein 2 (48kD) | IR |
| 137 | X70394 | ZNF146 | zinc finger protein 146 | IR |
| 138 | AF041259 | ZNF217 | zinc finger protein 217 | IR |
| 139 | M94314 | RPL24 | ribosomal protein L24 | IR |
| 140 | U09510 | GARS | glycyl-tRNA synthetase | UV |
| 141 | AF042384 | BC-2 | putative breast adenocarcinoma marker (32kD) | IR |
| 142 | HG1800-HT1823 | | | IR |
| 143 | U96915 | SAP18 | sin3-associated polypeptide, 18kD | IR |
| 144 | M13934 | | ribosomal protein S14 | IR |
| 145 | Z11697 | CD83 | CD83 antigen (activated B lymphocytes, immunoglobulin superfamily) | IR |
| 146 | U19599 | BAX | BCL2-associated X protein | IR |
| 147 | AA527880 | | | IR |
| 148 | U48734 | ACTN4 | actinin, alpha 4 | UV |
| 149 | U14972 | RPS10 | ribosomal protein S10 | IR |
| 150 | D00760 | PSMA2 | proteasome (prosome, macropain) subunit, alpha type, 2 | IR |
| 151 | M86667 | NAP1L1 | nucleosome assembly protein 1-like 1 | UV |
| 152 | AF057557 | TOSO | regulator of Fas-induced apoptosis | IR |
| 153 | U59309 | FH | fumarate hydratase | UV |
| 154 | AL049701 | KIAA0471 | KIAA0471 gene product | UV |
| 155 | AB029014 | KIAA1091 | KIAA1091 protein | UV |
| 156 | D23661 | RPL37 | ribosomal protein L37 | IR |
| 157 | U03106 | CDKN1A | cyclin-dependent kinase inhibitor 1A (p21, Cip1) | UV |
| 158 | AC004770 | | | UV |
| 159 | AF037643 | RPL12 | ribosomal protein L12 | IR |
| 160 | U07424 | FARSL | phenylalanine-tRNA synthetase-like | UV |
| 161 | AA806768 | | Homo sapiens phorbolin I protein (PBI) mRNA, complete cds | UV |
| 162 | L49380 | ZNF162 | zinc finger protein 162 | UV |
| 163 | AL050366 | OGT | O-linked N-acetylglucosamine (GlcNAc) transferase (UDP-N-acetylglucosamine: polypeptide-N-acetylglucosaminyl transferase) | IR |
| 164 | L12723 | HSPA4 | heat shock 70kD protein 4 | IR |
| 165 | M13932 | RPS17 | ribosomal protein S17 | IR |
| 166 | U51004 | HINT | histidine triad nucleotide-binding protein | IR |
| 167 | M64716 | RPS25 | ribosomal protein S25 | IR |
| 168 | Z11697 | CD83 | CD83 antigen (activated B lymphocytes, immunoglobulin superfamily) | UV |
| 169 | N98670 | | | IR |
| 170 | U14966 | RPL5 | ribosomal protein L5 | IR |
| 171 | D13643 | DHCR24 | 24-dehydrocholesterol reductase | UV |
| 172 | D21262 | NOLC1 | nucleolar and coiled-body phosphprotein 1 | IR |
| 173 | AC005943 | | | UV |
| 174 | AF044671 | GABARAP | GABA(A) receptor-associated protein | IR |
| 175 | U54559 | EIF3S3 | eukaryotic translation initiation factor 3, subunit 3 (gamma, 40kD) | IR |
| 176 | J04130 | SCYA4 | small inducible cytokine A4 (homologous to mouse Mip-1b) | IR |
| 177 | U19599 | BAX | BCL2-associated X protein | UV |
| 178 | X57206 | ITPKB | inositol 1,4,5-trisphosphate 3-kinase B | UV |
| 179 | D87446 | KIAA0257 | KIAA0257 protein | UV |
| 180 | T58471 | UQCR | ubiquinol-cytochrome c reductase (6.4kD) subunit | IR |
| 181 | U02570 | ARHGAP1 | Rho GTPase activating protein 1 | UV |
| 182 | X51688 | CCNA2 | cyclin A2 | UV |
| 183 | D31885 | ARL6IP | ADP-ribosylation factor-like 6 interacting protein | UV |
| 184 | AI541336 | NDUFS5 | NADH dehydrogenase (ubiquinone) Fe-S protein 5 (15kD) (NADH-coenzyme Q reductase) | IR |

TABLE 3-continued

| Rank | Accession | Symbol | Name | IR or UV response |
|---|---|---|---|---|
| 185 | V00567 | B2M | beta-2-microglobulin | IR |
| 186 | M86737 | SSRP1 | structure specific recognition protein 1 | UV |
| 187 | D80005 | C9orf10 | C9orf10 protein | UV |
| 188 | AF017789 | TAF2S | TATA box binding protein (TBP)-associated factor, RNA polymerase II, S, 150kD | IR |
| 189 | AB014458 | USP1 | ubiquitin specific protease 1 | UV |
| 190 | X63469 | GTF2E2 | general transcription factor IIE, polypeptide 2 (beta subunit, 34kD) | IR |
| 191 | M55914 | ENO1 | enolase 1, (alpha) | IR |
| 192 | Y00451 | ALAS1 | aminolevulinate, delta-, synthase 1 | UV |
| 193 | AF046001 | ZNF207 | zinc finger protein 207 | UV |
| 194 | D29643 | DDOST | dolichyl-diphosphooligosaccharide-protein glycosyltransferase | IR |
| 195 | U29344 | FASN | fatty acid synthase | UV |
| 196 | L13848 | DDX9 | DEAD/H (Asp-Glu-Ala-Asp/His) box polypeptide 9 (RNA helicase A, nuclear DNA helicase II; leukophysin) | UV |
| 197 | J00314 | TUBB | tubulin, beta polypeptide | IR |
| 198 | X71874 | | | UV |
| 199 | D90070 | PMAIP1 | phorbol-12-myristate-13-acetate-induced protein 1 | IR |
| 200 | X64330 | ACLY | ATP citrate lyase | UV |
| 201 | M94362 | LMNB2 | lamin B2 | IR |
| 202 | M23114 | ATP2A2 | ATPase, Ca++ transporting, cardiac muscle, slow twitch 2 | UV |
| 203 | J03040 | SPARC | secreted protein, acidic, cysteine-rich (osteonectin) | IR |
| 204 | X64229 | DEK | DEK oncogene (DNA binding) | IR |
| 205 | J03826 | FDXR | ferredoxin reductase | UV |
| 206 | U51698 | DED | apoptosis antagonizing transcription factor | UV |
| 207 | Z37166 | BAT1 | HLA-B associated transcript 1 | IR |
| 208 | X62744 | HLA-DMA | major histocompatibility complex, class II, DM alpha | IR |
| 209 | U28686 | RBM3 | RNA binding motif protein 3 | UV |
| 210 | D00860 | PRPS1 | phosphoribosyl pyrophosphate synthetase 1 | UV |
| 211 | L76200 | GUK1 | guanylate kinase 1 | IR |
| 212 | AB011118 | KIAA0546 | KIAA0546 protein | IR |
| 213 | L08895 | MEF2C | MADS box transcription enhancer factor 2, polypeptide C (myocyte enhancer factor 2C) | IR |
| 214 | D38551 | RAD21 | RAD21 homolog | IR |
| 215 | M32578 | HLA-DRB1 | major histocompatibility complex, class II, DR beta 1 | UV |
| 216 | X66079 | SPIB | Spi-B transcription factor (Spi-1/PU.1 related) | IR |
| 217 | U03398 | TNFSF9 | tumor necrosis factor (ligand) superfamily, member 9 | UV |
| 218 | Y13936 | PPM1G | protein phosphatase 1G (formerly 2C), magnesium-dependent, gamma isoform | IR |
| 219 | X15940 | RPL31 | ribosomal protein L31 | IR |
| 220 | J04031 | MTHFD1 | methylenetetrahydrofolate dehydrogenase (NADP+ dependent), methenyltetrahydrofolate cyclohydrolase, formyltetrahydrofolate synthetase | UV |
| 221 | AI032612 | SNRPF | small nuclear ribonucleoprotein polypeptide F | IR |
| 222 | AJ245416 | LSM2 | U6 snRNA-associated Sm-like protein | IR |
| 223 | L25931 | LBR | lamin B receptor | UV |
| 224 | J05614 | | | IR |
| 225 | AL050265 | TARDBP | TAR DNA binding protein | UV |
| 226 | X04366 | CAPN1 | calpain 1, (mu/l) large subunit | UV |
| 227 | AL050161 | | | IR |
| 228 | D42084 | METAP1 | methionyl aminopeptidase 1 | IR |
| 229 | U90878 | PDLIM1 | PDZ and LIM domain 1 (elfin) | IR |
| 230 | AL080109 | KIAA0618 | KIAA0618 gene product | IR |
| 231 | U94319 | PSIP2 | PC4 and SFRS1 interacting protein 2 | IR |
| 232 | L15189 | HSPA9B | heat shock 70kD protein 9B (mortalin-2) | UV |
| 233 | X80199 | MLN51 | MLN51 protein | IR |
| 234 | AL050060 | DKFZP566H073 | DKFZP566H073 protein | UV |
| 235 | X59543 | RRM1 | ribonucleotide reductase M1 polypeptide | UV |
| 236 | AB019987 | SMC4L1 | SMC4 (structural maintenance of chromosomes 4)-like 1 | UV |
| 237 | J04977 | XRCC5 | X-ray repair complementing defective repair (double-strand-break rejoining; Ku autoantigen, 80kD) | UV |
| 238 | Y07969 | SSP29 | acidic protein rich in leucines | UV |
| 239 | U37690 | POLR2L | polymerase (RNA) II (DNA directed) polypeptide L (7.6kD) | IR |
| 240 | AB018328 | ALTE | Ac-like transposable element | IR |
| 241 | AI540925 | COX6A1 | cytochrome c oxidase subunit VIa polypeptide 1 | IR |
| 242 | HG1515-HT1515 | Btf3b | Transcription Factor Btf3b | IR |
| 243 | U87947 | EMP3 | epithelial membrane protein 3 | UV |
| 244 | AB028990 | KIAA1067 | KIAA1067 protein | IR |
| 245 | X55954 | RPL23 | ribosomal protein L23 | IR |
| 246 | X02994 | ADA | adenosine deaminase | UV |
| 247 | AB029038 | KIAA1115 | KIAA1115 protein | UV |

TABLE 3-continued

| Rank | Accession | Symbol | Name | IR or UV response |
|---|---|---|---|---|
| 248 | L29254 | | | IR |
| 249 | U05040 | | Homo sapiens far upstream element (FUSE) binding protein 1 (FUBP1), mRNA | UV |
| 250 | AF007140 | ILF3 | interleukin enhancer binding factor 3, 90kD | UV |
| 251 | X59303 | VARS2 | valyl-tRNA synthetase 2 | UV |
| 252 | AI345944 | NDUFB1 | NADH dehydrogenase (ubiquinone) 1 beta subcomplex, 1 (7kD, MNLL) | IR |
| 253 | U21689 | GSTP1 | glutathione S-transferase pi | IR |
| 254 | Z24459 | | | IR |
| 255 | U45878 | BIRC3 | baculoviral IAP repeat-containing 3 | UV |
| 256 | AF081280 | NPM3 | nucleophosmin/nucleoplasmin 3 | UV |
| 257 | Z25535 | NUP153 | nucleoporin 153kD | IR |
| 258 | D26579 | ADAM8 | a disintegrin and metalloproteinase domain 8 | IR |
| 259 | AF063308 | DEEPEST | mitotic spindle coiled-coil related protein | UV |
| 260 | S57212 | MEF2C | MADS box transcription enhancer factor 2, polypeptide C (myocyte enhancer factor 2C) | IR |
| 261 | Y00971 | PRPS2 | phosphoribosyl pyrophosphate synthetase 2 | UV |
| 262 | AF067656 | ZWINT | ZW10 interactor | UV |
| 263 | M91196 | ICSBP1 | interferon consensus sequence binding protein 1 | IR |
| 264 | AI033692 | BCRP1 | Breakpoint cluster region protein, uterine leiomyoma, 1; barrier to autointegration factor | UV |
| 265 | AL022326 | SYNGR1 | synaptogyrin 1 | IR |
| 266 | AF032885 | FOXO1A | forkhead box O1A (rhabdomyosarcoma) | UV |
| 267 | U03911 | MSH2 | mutS homolog 2 (colon cancer, nonpolyposis type 1) | UV |
| 268 | AL021154 | | | IR |
| 269 | AB011116 | KIAA0544 | KIAA0544 protein | IR |
| 270 | X17644 | GSPT1 | G1 to S phase transition 1 | UV |
| 271 | AI565760 | GABARAPL2 | GABA(A) receptor-associated protein-like 2 | IR |
| 272 | D87735 | RPL14 | ribosomal protein L14 | IR |
| 273 | U52112 | IRAK1 | interleukin-1 receptor-associated kinase 1 | UV |
| 274 | X04803 | | ubiquitin | IR |
| 275 | AI525834 | NPC2 | Niemann-Pick disease, type C2 gene | IR |
| 276 | M14333 | FYN | FYN oncogene related to SRC, FGR, YES | UV |
| 277 | Z97054 | UREB1 | upstream regulatory element binding protein 1 | UV |
| 278 | AB014609 | KIAA0709 | endocytic receptor (macrophage mannose receptor family) | UV |
| 279 | AI653621 | TXN | thioredoxin | UV |
| 280 | U24266 | ALDH4A1 | aldehyde dehydrogenase 4 family, member A1 | UV |
| 281 | M37583 | H2AFZ | H2A histone family, member Z | UV |
| 282 | J03805 | PPP2CB | protein phosphatase 2 (formerly 2A), catalytic subunit, beta isoform | UV |
| 283 | U51127 | IRF5 | interferon regulatory factor 5 | UV |
| 284 | M22806 | P4HB | prolyl 4-hydroxylase beta-subunit and disulfide isomerase | UV |
| 285 | D11086 | IL2RG | interleukin 2 receptor, gamma (severe combined immunodeficiency) | UV |
| 286 | AF000982 | DDX3 | DEAD/H (Asp-Glu-Ala-Asp/His) box polypeptide 3 | UV |
| 287 | U86602 | EBNA1BP2 | EBNA1-binding protein 2 | UV |
| 288 | AF000231 | RAB11A | RAB11A, member RAS oncogene family | UV |
| 289 | L23959 | TFDP1 | transcription factor Dp-1 | UV |
| 290 | AB020713 | KIAA0906 | KIAA0906 protein | UV |
| 291 | X59871 | TCF7 | transcription factor 7 (T-cell specific, HMG-box) | UV |
| 292 | AA310786 | | Homo sapiens cDNA: FLJ23602 fis, clone LNG15735 | IR |
| 293 | U15085 | HLA-DMB | major histocompatibility complex, class II, DM beta | IR |
| 294 | D80001 | KIAA0179 | KIAA0179 protein | IR |
| 295 | HG4074-HT4344 | Rad2 | Rad2 | UV |
| 296 | AA648295 | CBX3 | chromobox homolog 3 (HP1 gamma) | UV |
| 297 | Y13936 | PPM1G | protein phosphatase IG (formerly 2C), magnesium-dependent, gamma isoform | UV |
| 298 | D49489 | P5 | protein disulfide isomerase-related protein | UV |
| 299 | AJ012590 | H6PD | hexose-6-phosphate dehydrogenase (glucose 1-dehydrogenase) | IR |
| 300 | D16431 | HDGF | hepatoma-derived growth factor (high-mobility group protein 1-like) | IR |
| 301 | AA527880 | | | IR |
| 302 | AI525665 | COX8 | cytochrome c oxidase subunit VIII | IR |
| 303 | U19765 | ZNF9 | zinc finger protein 9 (a cellular retroviral nucleic acid binding protein) | UV |
| 304 | M74491 | ARF3 | ADP-ribosylation factor 3 | UV |
| 305 | AF039397 | | | UV |
| 306 | X67951 | PRDX1 | peroxiredoxin 1 | IR |
| 307 | AB005047 | SH3BP5 | SH3-domain binding protein 5 (BTK-associated) | IR |
| 308 | S75463 | TUFM | Tu translation elongation factor, mitochondrial | UV |
| 309 | M63904 | GNA15 | guanine nucleotide binding protein (G protein), alpha 15 (Gq class) | UV |

TABLE 3-continued

| Rank | Accession | Symbol | Name | IR or UV response |
|---|---|---|---|---|
| 310 | D42084 | METAP1 | methionyl aminopeptidase 1 | UV |
| 311 | W28979 | FLJ20452 | hypothetical protein FLJ20452 | IR |
| 312 | M59465 | TNFAIP3 | tumor necrosis factor, alpha-induced protein 3 | IR |
| 313 | M26004 | CR2 | complement component, receptor 2 | IR |
| 314 | X04106 | CAPNS1 | calpain, small subunit 1 | IR |
| 315 | Z14000 | RING1 | ring finger protein 1 | UV |
| 316 | AF044671 | GABARAP | GABA(A) receptor-associated protein | UV |
| 317 | D13627 | CCT8 | chaperonin containing TCP1, subunit 8 (theta) | UV |
| 318 | D21853 | KIAA0111 | KIAA0111 gene product | UV |
| 319 | HG662-HT662 | | Small Rna-Associated Protein | IR |
| 320 | AI087268 | SNRPC | small nuclear ribonucleoprotein polypeptide C | IR |
| 321 | D80000 | SMC1L1 | SMC1 (structural maintenance of chromosomes 1)-like 1 | UV |
| 322 | L31584 | EBI 1 | G protein-coupled receptor | UV |
| 323 | M33336 | PRKAR1A | protein kinase, cAMP-dependent, regulatory, type I, alpha (tissue specific extinguisher 1) | UV |
| 324 | D14812 | KIAA0026 | MORF-related gene X | UV |
| 325 | D11139 | TIMP1 | tissue inhibitor of metalloproteinase 1 (erythroid potentiating activity, collagenase inhibitor) | UV |
| 326 | M65028 | HNRPAB | heterogeneous nuclear ribonucleoprotein A/B | UV |
| 327 | AB023154 | KIAA0937 | KIAA0937 protein | UV |
| 328 | AA149486 | COX17 | COX17 homolog, cytochrome c oxidase assembly protein | IR |
| 329 | Y00371 | hsc70 | 71kd heat shock cognate protein | UV |
| 330 | X95808 | ZNF261 | zinc finger protein 261 | IR |
| 331 | M64595 | RAC2 | ras-related C3 botulinum toxin substrate 2 (rho family, small GTP binding protein Rac2) | IR |
| 332 | D50405 | HDAC1 | histone deacetylase 1 | UV |
| 333 | X95384 | UK114 | translational inhibitor protein p14.5 | UV |
| 334 | M93311 | MT3 | metallothionein 3 (growth inhibitory factor (neurotrophic)) | IR |
| 335 | M13792 | ADA | adenosine deaminase | UV |
| 336 | D90070 | PMAIP1 | phorbol-12-myristate-13-acetate-induced protein 1 | UV |
| 337 | AF047436 | ATP5J2 | ATP synthase, H+ transporting, mitochondrial F0 complex, subunit f, isoform 2 | UV |
| 338 | U24152 | PAK1 | p21/Cdc42/Rac1-activated kinase 1 (yeast Ste20-related) | UV |
| 339 | U46692 | | cystatin B | IR |

In certain embodiments, any one or more of the genes/proteins in the prepared expression profile are from Table 3, above, where the expression profile may include expression data for 5, 10, 20, 25, 50, 100 or more of, including all of, the genes/proteins listed in Table 3, above.

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained.

The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue harvested from a subject to be diagnosed, e.g., via blood drawing, biopsy of tissue, using standard protocols, where cell types or tissues from which such nucleic acids may be generated include any tissue in which the expression pattern of the to be determined phenotype exists. Cells may be cultured prior to analysis.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acid provides information regarding expression for each of the genes that have been probed, where the expression information is in terms of whether or not the gene is expressed and, typically, at what level, where the expression data, i.e., expression profile, may be both qualitative and quantitative.

Alternatively, non-array based methods for quantitating the levels of one or more nucleic acids in a sample may be employed, including quantitative PCR, and the like.

Where the expression profile is a protein expression profile, any convenient protein quantitation protocol may be employed, where the levels of one or more proteins in the assayed sample are determined. Representative methods include, but are not limited to; proteomic arrays, flow cytometry, standard immunoassays, etc.

Following obtainment of the expression profile from the sample being assayed, the expression profile is compared with a reference or control profile to make a diagnosis regarding the radiation toxicity susceptibility phenotype of the cell or tissue from which the sample was obtained/derived. Typically a comparison is made with a set of cells from the same source, which has not been exposed to radiation. Additionally, a reference or control profile may be a profile that is obtained from a cell/tissue known to have the susceptible phenotype, and therefore may be a positive reference or control profile. In addition, a reference/control profile may be from a cell/tissue known to not have the susceptibility phenotype, and therefore be a negative reference/control profile.

In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The difference values, i.e. the difference in expression in the presence and absence of radiation may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

A statistical analysis step is then performed to obtain the weighted contribution of the set of predictive genes. Nearest shrunken centroids analysis, is applied as described in Tibshirani et al. (2002) P.N.A.S. 99:6567-6572 to compute the centroid for each class, then compute the average squared distance between a given expression profile and each centroid, normalized by the within-class standard deviation.

To perform a shrunken centroids analysis, let $x_{ik}$ be the expression for genes $i=1, 2, \ldots p$ and samples $j=1, 2, \ldots n$. Classes are $1, 2, \ldots K$, and $C_k$ is indices of the $n_k$ samples in class k. The ith component of the centroid for class k is $\bar{x}_{ik} = \Sigma j \in C_k x_{ij} n_k / n_k$ the mean expression value in class k for gene i; the ith component of the overall centroid is $\bar{x}_i = \Sigma_j = 1 x_{ij/n}{}^n$. In words, one shrinks the class centroids toward the overall centroids after standardizing by the within-class standard deviation for each gene. This standardization has the effect of giving higher weight to genes whose expression is stable within samples of the same class.

$$d_{ik} = \frac{\bar{x}_{ik} - \bar{x}_i}{m_k \cdot (s_i + s_o)}, \quad [1]$$

where $s_i$ is the pooled within-class standard deviation for gene i:

$$s_i^2 = \frac{1}{n-K} \sum_k \sum_{j \in C_k} (x_{ij} - \bar{x}_{ik})^2 \quad [2]$$

and $m_k = \sqrt{1/n_k + 1/n}$ makes $m_k \cdot s_i$ equal to the estimated standard error of the numerator in $d_{ik}$. In the denominator, the value $s_o$ is a positive constant (with the same value for all genes), included to guard against the possibility of large $d_{ik}$ values arising by chance from genes with low expression levels. $s_o$ is set to be equal to the median value of the $s_i$ over the set of genes.

Thus $d_{ik}$ is a t statistic for gene i, comparing class k to the overall centroid. Eq. 1 can be rewritten as $$\bar{x}_{ik} = \bar{x}_i + m_k(s_i + s_o)d_{ik} \quad [3]$$

This method shrinks each $d_{ik}$ toward zero, giving $d'_{ik}$ and yielding shrunken centroids or prototypes $$\bar{x}'_{ik} = \bar{x}_i + m_k(s_i + s_o)d'_{ik} \quad [4]$$

The shrinkage is called soft thresholding: each $d_{ik}$ is reduced by an amount $\Delta$ in absolute value and is set to zero if its absolute value is less than zero. Algebraically, soft thresholding is defined by $$d'_{ik} = \text{sign}(d_{ik})(|d_{ik}| - \Delta)_+ \quad [5]$$

where + means positive part ($t_+ = t$ if $t>0$ and zero otherwise). Because many of the $\bar{x}_{ik}$ values will be noisy and close to the overall mean $\bar{x}_i$, soft thresholding produces more reliable estimates of the true means. This method has the desirable property that many of the components (genes) are eliminated from the class prediction as the shrinkage parameter $\Delta$ is increased. Specifically, if for a gene i, $d_{ik}$ is shrunken to zero for all classes k, then the centroid for gene i is $\bar{x}_i$, the same for all classes. Thus gene i does not contribute to the nearest-centroid computation.

Depending on the type and nature of the reference/control profile(s) to which the obtained expression profile is compared, the above comparison step yields information as to whether a patient is susceptible to toxicity after exposure to antiproliferative therapy. As such, the above comparison step can yield a positive/negative determination of a susceptible phenotype of an assayed cell/tissue.

Figure 3:
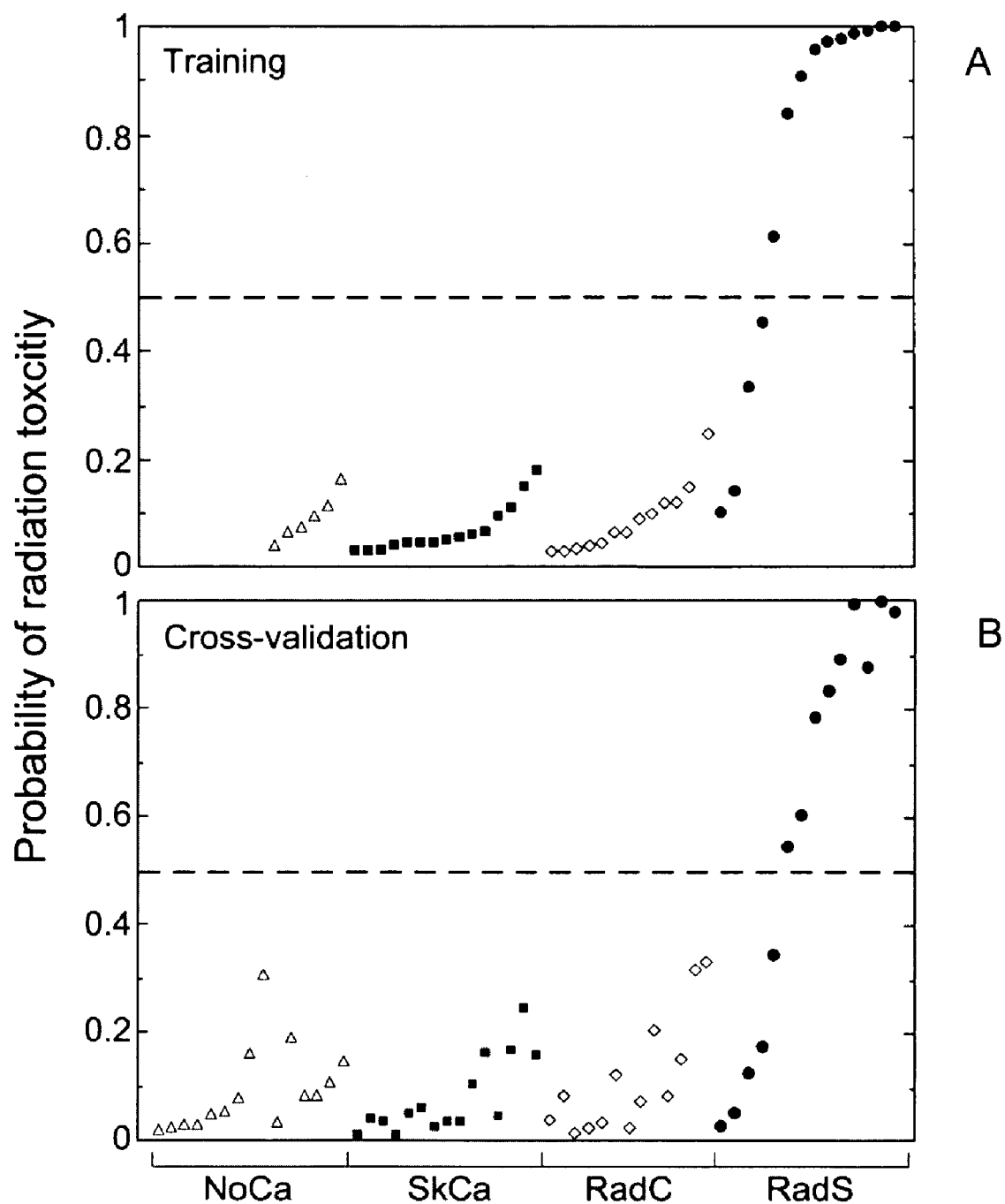
FIGS. 3A-3B. Predicting radiation toxicity from transcriptional responses to IR and UV. The plots show predictions for 15 subjects with no cancer (NoCa), 15 patients with skin cancer (SkCa), 13 control cancer patients without toxicity from radiation therapy (RadC), and 14 radiation sensitive cancer patients (RadS). HAT/NSC identified 24 predictive genes represented by 25 probe sets. The IR and UV responses were used to compute the probability of toxicity for each subject. The dotted lines indicate probability of 0.5, the prospectively defined cutoff for predicting radiation toxicity. The upper panel shows probabilities for radiation toxicity calculated from the full 48-sample training set. To avoid selection bias (see Ambroise and McLachlan (2002) *P.N.A.S.* 99:6562-6566), the 9 NoCa subjects were excluded from the training set because these subjects were used to identify the IR and UV-responsive genes. The lower panel shows probabilities calculated from 14-fold cross-validation as described in the text. The 9 NoCa subjects were excluded from the training sets, but included for cross-validation.

The prediction of susceptibility is probabilistically defined, where the cut-off for predicted susceptibility may be empirically derived, for example as shown in FIG. 3. In one embodiment of the invention, a probability of about 0.4 may be used to distinguish between susceptible and non-susceptible patients, more usually a probability of about 0.5, and may utilize a probability of about 0.6 or higher. A "high" probability may be at least about 0.75, at least about 0.7, at least about 0.6, or at least about 0.5. A "low" probability may be not more than about 0.25, not more than 0.3, or not more than 0.4. In many embodiments, the above-obtained information about the cell/tissue being assayed is employed to predict whether a host, subject or patient is treated with a therapy of interest, e.g. treatment with ionizing radiation, exposure to a chemotherapeutic agent etc., and to optimize the dose therein.

Databases of Expression Profiles

Also provided are databases of expression profiles of phenotype determinative genes. Such databases will typically comprise expression profiles of various cells/tissues having susceptible phenotypes, negative expression profiles, etc., where such profiles are further described below.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

Reagents and Kits

Also provided are reagents and kits thereof for practicing one or more of the above-described methods. The subject reagents and kits thereof may vary greatly. Reagents of interest include reagents specifically designed for use in production of the above described expression profiles of phenotype determinative genes.

One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In certain embodiments, the number of genes that are from Table 3 that is represented on the array is at least 10, usually at least 25, and may be at least 50, 100, up to including all of the genes listed in Table 3, preferably utilizing the top ranked set of genes. The subject arrays may include only those genes that are listed in Table 3, or they may include additional genes that are not listed in Table 3. Where the subject arrays include probes for such additional genes, in certain embodiments the number % of additional genes that are represented does not exceed about 50%, usually does not exceed about 25%. In many embodiments where additional "non-Table 3" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are predictive genes.

Another type of reagent that is specifically tailored for generating expression profiles of phenotype determinative genes is a collection of gene specific primers that is designed to selectively amplify such genes, for use in quantitative PCR and other quantitation methods. Gene specific primers and methods for using the same are described in U.S. Pat. No. 5,994,076, the disclosure of which is herein incorporated by reference. Of particular interest are collections of gene specific primers that have primers for at least 10 of the genes listed in Table 3, above, often a plurality of these genes, e.g., at least 25, and may be 50, 100 or more to include all of the genes listed in Table 3. The subject gene specific primer collections may include only those genes that are listed in Table 3, or they may include primers for additional genes that are not listed in Table 3. Where the subject gene specific primer collections include primers for such additional genes, in certain embodiments the number % of additional genes that are represented does not exceed about 50%, usually does not exceed about 25%. In many embodiments where additional "non-Table 3" genes are included, a great majority of genes in the collection are phenotype determinative genes, where by great majority is meant at least about 75%, usually at least about 80% and sometimes at least about 85, 90, 95% or higher, including embodiments where 100% of the genes in the collection are predictive genes.

The kits of the subject invention may include the above described arrays and/or gene specific primer collections. The kits may further include a software package for statistical analysis of one or more phenotypes, and may include a reference database for calculating the probability of susceptibility. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Method of Analyzing Genes for Predictive Value

In another aspect of the invention, methods are provided for identifying genes and proteins that are predictive of a phenotype of interest. Such analytical methods provide a set of molecules whose pattern of expression yields information about a phenotype of interest. The molecules may be transcriptional responses, expression of a protein, post-translational protein modification, e.g. cleavage, phosphorylation and dephosporylation, glycosylation, etc.

The pattern of expression may be basal levels of expression in a target cell type, e.g. expression of a gene in a cancer cell, differential expression of a gene in a normal v. a cancer cell, expression of a gene during a specific developmental stage, basal phosphorylation of a protein in a cell, and the like. The pattern of expression may also be in response to a treatment of interest, e.g. exposure to radiation, exposure to a therapeutic agent, exposure to cytokines, response of cells in a mixed lymphocyte reaction, and the like. The shrunken centroid analysis described above may be used to determine an expression profile for any phenotype of interest.

The phenotype of interest may be susceptibility to toxicity, response to a therapeutic regimen or agent, development of autoimmune disease, development of graft rejection, development of graft v. host disease, distinction of heterogeneity in an early stage of cancer, e.g. prediction of probable course of disease, and the like.

To obtain the set of predictive genes, initially cohorts are gathered for the phenotype of interest, e.g. patients suffering from a disease of interest, responders and non-responders to a treatment of interest, and the like. One or more cohorts are gathered for the phenotype of interest, and one or more for a control, preferably a matched control group, according to methods known in the art.

An expression profile for the trait to be examined is made. Convenient methods for examining large groups of genes include hybridization to microarrays, as discussed above and in the examples. Alternatively, proteomics arrays may be used to determine protein profiles, antibody array can be used to detect the presence of epitopes of interest in a sample, various methods known in the art for quantitative hybridization of a nucleic acid may be used, and the like. As discussed above, the basal expression level may be taken, or a response to a particular stimulus. In many cases it is desirable to determine a difference in expression between a control and a test sample. The expression may be normalized a control, to expression of a housekeeping gene or genes, etc., as known in the art.

Many phenotypes of interest are actually the result of different underlying genotypes, where a heterogeneous response over a patient population can make analysis difficult. To address the problem of heterogeneity, the following heterogeneity-associated transformation (HAT) is performed, using the following equation:

$$x'(i) = [x(i) - \bar{x}_c(i)]^2 \qquad [6]$$

where x(i) is the change in expression for gene i, and $\bar{x}_c(i)$ is the average change in expression for gene i among the control samples. HAT generates equivalent values for changes in gene expression that are blunted in some cases and enhanced in others, and hence can capture heterogeneous abnormalities among the radiation sensitive patients. Genes with divergent transcriptional responses might be overlooked by comparing the average response of controls to the average response, but are successfully identified after transforming the data.

After transforming the data, nearest shrunken centroid analysis is performed, as described above and in Tibshirani et al. (2002), supra. The centroid of gene expression for a class of samples is defined as a multi-component vector, in which each component is the expression of a gene averaged over the samples. Samples are then classified by proximity to the nearest centroid. In order to verify the prediction, it is desirable to test profiles against an independent set of samples, or with cross-validation.

The probability of a specific outcome is then calculated. The cut-off for a particular diagnosis will be determined empirically, based on the specific set of data, and may be modeled to include the weighted probability for rare events.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

The following examples are offered by way of illustration and not by way of limitation.

Experimental

Toxicity from radiation therapy is a grave problem for cancer patients, and methods are needed for predicting its occurrence. Microarrays were used to analyze abnormal transcriptional responses to DNA damage in cultured lymphocytes. A transformation of the data was devised to account for the possibility that toxicity can arise from defects in different pathways. The risk of toxicity was then computed for each patient using nearest shrunken centroids, a method that identifies predictive genes. Transcriptional responses in 24 genes predicted radiation toxicity in 9 of 14 patients with no false positives among 43 controls. Some patients had defective responses to ionizing radiation, while others had defective responses to both ultraviolet and ionizing radiation. This approach has the potential to predict toxicity from ionizing radiation and other anticancer agents, enabling physicians to design a safe treatment plan for each patient.

Materials and Methods

Patient cell lines. Subjects were enrolled with informed consent between 1997 and 2002 in accordance with Stanford regulations for human subjects research. Radiation toxicity was graded according to the RTOG Acute and Late Radiation Morbidity Scoring Criteria. Radiation therapy patients donated peripheral blood samples at least 2 months following completion of treatment and resolution of any toxicity. Lymphoblastoid cell lines were established by immortalization of peripheral blood B-lymphocytes with Epstein-Barr virus from the B95-8 monkey cell line. Cells were grown in RPMI 1640 (Gibco) with 15% heat inactivated fetal bovine serum, 1% penicillin/streptomycin, and 2 mM glutamine and stored in liquid nitrogen.

Treatment of cells with UV and IR. Lymphoblastoid cells were subjected to mock, UV, and IR treatment. For UV treatment, $5\times10^7$ cells were suspended in PBS at $6\times10^5$ cells/ml to ensure uniform exposure to UV. Cells subjected to mock and IR treatment were also suspended in PBS during this period to ensure similar treatment. For UV treatment, cells were exposed for 15 sec to a germicidal lamp at a fluence of 0.67 $J/m^2/sec$ to deliver a 10 $J/m^2$ dose, seeded at $3\times10^5$ cells/ml in fresh media, and harvested for RNA 24 hrs later. For IR treatment, $4\times10^7$ cells were exposed to 5 Gy IR 20 hrs after the PBS wash and harvested for RNA 4 hrs later.

Microarray hybridization. Total RNA was labeled with biotin and hybridized to a U95A_v2 GeneChip® microarray, according to manufacturer's protocols (Affymetrix, Santa Clara, Calif.). The expression level for each gene was calculated by Affymetrix GeneChip Microarray Analysis Suite software version 4.0. To account for differences in hybridization between different chips, data from hybridizations were scaled to the average of all data sets, as described by Tusher et al. (2001) Proc. Natl. Acad. Sci. USA; 98:5116-5121.

Analysis of microarray data. The data was in the form of change in gene expression, computed for each individual as the difference in expression before and after exposure to UV or IR. Analyses were based on changes in gene expression, because this was less sensitive to variation among different individuals than the basal or induced levels of expression. Thus, we used the paired data option in Significance Analysis of Microarrays (SAM), which ranks genes by change in expression relative to the standard deviation in multiple samples. IR-responsive and UV-responsive genes were identified using data from 9 normal individuals." The false discovery rate (FDR) is the percentage of genes falsely called significant when the change in gene expression for each individual is randomly chosen to be left unaltered or multiplied by −1. Responsive genes were obtained by choosing a threshold corresponding to an FDR of 10%.

The nearest shrunken centroid (NSC) classifier was applied to the radiation toxicity and control classes (Tibshirani et al. (2002) Proc. Natl. Acad. Sci. USA 99:6567-6572). The centroid for a class of samples was defined as a multi-component vector, in which each component was the expression of a predictive gene averaged over the samples in that class. NSC shrinks the class centroids towards the overall centroid after normalizing by the within-class standard deviation for each gene. The probability for radiation toxicity associated with an expression profile was computed from its distances to the radiation toxicity and control centroids.

The accuracy of a supervised classifier such as NSC may appear to be high when applied to the training samples, i.e., the samples used to define the centroids. However, this is not statistically valid. The number of genes is much greater than the number of samples in microarray experiments, providing many opportunities to find genes with expression patterns that correlate with the class of interest. Thus, supervised classifiers are susceptible to overfitting, and their accuracy must be tested by cross-validation on samples not used for training Ambroise and McLachlan (2002) Proc Natl Acad Sci USA; 99:6562-6566.

We subjected NSC to 14-fold cross-validation by dividing the samples into 14 subsets. Each subset contained one radiation sensitive patient plus 2 or 3 controls selected from the radiation controls, skin cancer patients, and non-cancer controls. We withheld one subset and trained NSC on the remaining samples to identify a set of predictive genes, which defined a radiation sensitive centroid and a control centroid. Each sample from the withheld subset was classified by its proximity to the nearest centroid. This protocol was repeated for each of the 14 subsets until every sample was classified. To avoid biasing our predictions, samples from the 9 subjects analyzed by SAM were excluded as training samples for NSC, but were assigned probabilities for radiation toxicity.

Hierarchical clustering (Eisen et al. (1998) Proc. Natl. Acad. Sci. USA; 95:14863-14868) used centered Pearson correlation and complete linkage clustering, and was displayed with TreeView. Biological functions were assigned from the literature and the SOURCE database.

Results

Radiation sensitive patients and controls. Fourteen radiation therapy patients were enrolled after suffering unusual levels of radiation toxicity within one month of treatment, as judged by a faculty member in the Department of Radiation Oncology at Stanford. Toxicity was severe enough so that 11 of these 14 patients required interruption or early termination of treatment. These interventions helped limit the reported toxicities to grades 2 and 3. Thirteen patients with radiation toxicity limited to grades 0 or 1 were recruited as controls. We attempted to match this patient group to the radiation sensitive group by radiation field and dose, tumor type, gender, and concurrent chemotherapy (Table 4). The average age of the radiation control patients was 59 years ±13 years, while the average age of the radiation sensitive patients was 51 years ±11 years. Since the risk of radiation toxicity increases with age (Turesson et al. (1996) Int J Radiat Oncol Biol Phys; 36:1065-75), the younger age of the radiation sensitive patients was protective and should enhance the validity of our results. This study incorporated significant heterogeneity in radiation treatments. Importantly, the radiation sensitive group was matched to the radiation control group. This facilitated our goal to find genes that predicted acute toxicity, independently of the underlying tumor or site of treatment.

TABLE 4

Clinical characteristics of radiation therapy patients

| Age/gender/diagnosis | | Patient | Reaction | Grade | Radiation/concurrent chemotherapy |
|---|---|---|---|---|---|
| *Radiation sensitive patients* | | | | | |
| 37F | breast cancer | RadS4* | skin | 3‡ | 45 Gy to breast |
| 49F | breast cancer | RadS14 | skin | 2‡ | 50 Gy to breast, 10 Gy boost/cytoxan, 5-FU |
| 53F | breast cancer | RadS12 | skin | 2‡ | 55 Gy to breast |
| 65F | breast cancer | RadS1 | *skin | 3‡ | 45 Gy to breast |
| 37F | Hodgkin's disease | RadS10 | skin; breast cancer 20y later | 3‡ | 40 Gy mantle field, 10 Gy neck boost |
| 50M | Hodgkin's disease | RadS6 | skin; stroke 8y later | 3 | 44 Gy mantle field |
| 67M | Hodgkin's disease | RadS8 | pneumonitis | 2‡ | 43 Gy mantle field, 36 Gy spade field |
| 57M | low grade lymphoma | RadS7 | mucositis; osteonecrosis of | 3‡ | 50 Gy to mandible & neck, 45 Gy to hip, hip & jaw, cystitis 10y later |
| 60M | low grade lymphoma | RadS2 | *skin | 3† | 31 Gy to lacrimal glands in both orbits |
| 41M | cancer of tongue | RadS3 | *mucositis | 3‡ | 70 Gy to tongue/tpz, cisplatin, 5-FU |
| 45M | salivary gland cancer | RadS9 | skin, mucositis | 3‡ | 40 Gy to oral cavity, 48 Gy to neck, 12 Gy to tongue/cisplatin, 5-FU |
| 67F | endometrial cancer | RadS13 | diarrhea | 3† | 42 Gy to pelvis |
| 52F | orbital pseudotumor | RadS11 | orbital edema | 2 | 31 Gy to orbit |
| 33F | brainstem AVM | RadS5 | *cerebral edema | 3 | 18 Gy stereotactic radiation to brainstem |
| *Radiation control patients* | | | | | |
| 45F | breast cancer | RadC8 | skin | 1 | 50 Gy to chest wall |
| 59F | breast cancer | RadC7 | skin | 1 | 50 Gy to breast, 10 Gy boost |
| 65F | breast cancer | RadC9 | skin | 1 | 50 Gy to breast, 10 Gy boost |
| 73F | breast cancer | RadC12 | skin | 1 | 50 Gy to breast |
| 78F | breast cancer | RadC13 | skin | 1 | 50 Gy to breast, 10 Gy boost |
| 39F | Hodgkin's disease | RadC1 | none | 0 | 44 Gy total lymphoid irradiation |
| 49F | Hodgkin's disease | RadC4 | none | 0 | 44 Gy mantle field |
| 46M | mixed cell lymphoma | RadC2 | none | 0 | 36 Gy to para-aortic & inguinal nodes, 31 Gy to orbital recurrence |
| 63M | large cell lymphoma | RadC3 | none | 0 | 36 Gy to parotid gland |
| 50F | salivary gland cancer | RadC5 | skin | 1 | 56 Gy to oropharynx |
| 56M | cancer of tonsil | RadC10 | skin, mouth dryness | 1 | 70 Gy to oropharynx/cisplatin, 5-FU |
| 70F | cancer of oropharynx | RadC6 | skin, mouth dryness | 1 | 66 Gy to oropharynx |
| 76M | cancer of tongue | RadC11 | skin, mouth dryness | 1 | 70 Gy to oropharynx/tpz, cisplatin, 5-FU |

*patient misclassified by NSC/HAT analysis of UV and IR responses
‡dose involved interruption of treatment
†dose involved early termination of treatment
Patients with reactions limited to grade 0 or 1 were included radiation controls (RadC). Patients with acute reactions (RadS) were enrolled as described in the text. Patients RadS6, RadS7, and RadS10 also suffered from grade 4 late reactions 8, 10, and 20 years following radiation therapy. Patients are numbered in the order in which they appear in FIGS. 1 and 3 from left to right.
Abbreviations:
AVM = arteriovenous malformation;
5-FU = 5-fluorouracil;
tpz = tirapazamine Cells were exposed to UV as well as IR to determine whether some radiation sensitive patients have a general defect in responding to DNA damage. Because skin cancer is associated with UV exposure, we enrolled 15 patients diagnosed with skin cancer before age 40 to serve as additional controls. A successful classification method should not assign a high risk for radiation toxicity to the skin cancer patients. Fifteen subjects without cancer were matched to the skin cancer patients for age, gender, and race. Because we recruited patients with early skin cancer, their average age was 38 years ±8 years, and the average age of the normal individuals was 31 years ±5 years, which were significantly younger than the age of the radiation sensitive patients. A total of 57 subjects were recruited for study.

Analysis by SAM and nearest shrunken centroids. To identify genes normally induced or repressed by IR or UV, we applied SAM to data from 9 subjects without a history of cancer. SAM identified 1491 IR-responsive genes and 2114 UV-responsive genes. We previously developed an enhancement of nearest centroids, nearest shrunken centroids (NSC), which successfully identified small sets of highly predictive genes for other classification problems. However, when we applied NSC to these IR and UV-responsive genes, classification required 1831 genes while generating 10 errors.

Heterogeneity-associated transformation. A new approach was needed to identify predictive genes. Radiation toxicity can arise from several different underlying genetic defects, generating divergent transcriptional responses. For example, one subset of radiation sensitive patients could have a defect in signaling through ATM, leading to a failure to activate p53 after IR and a blunted response in p53-induced genes. Another subset could have a defect in DNA repair, leading to prolonged activation of ATM and enhanced transcription of p53-induced genes.

To address the problem of heterogeneity, we performed the following heterogeneity-associated transformation (HAT)

$$x'(i) = [x(i) - \bar{x}_c(i)]^2 \qquad \text{Equation 1}$$

where x(i) is the change in expression for gene i, and $\bar{x}_c(i)$ is the average change in expression for gene i among the control samples. HAT generates similar values from changes in gene expression that are blunted in some cases or enhanced in others, and hence can capture heterogeneous abnormalities among the radiation sensitive patients. Simulations of microarray data demonstrated that NSC/HAT is more efficient than NSC alone in identifying genes with heterogeneous responses, but less efficient in identifying genes with homogeneous responses.

Figure 2:
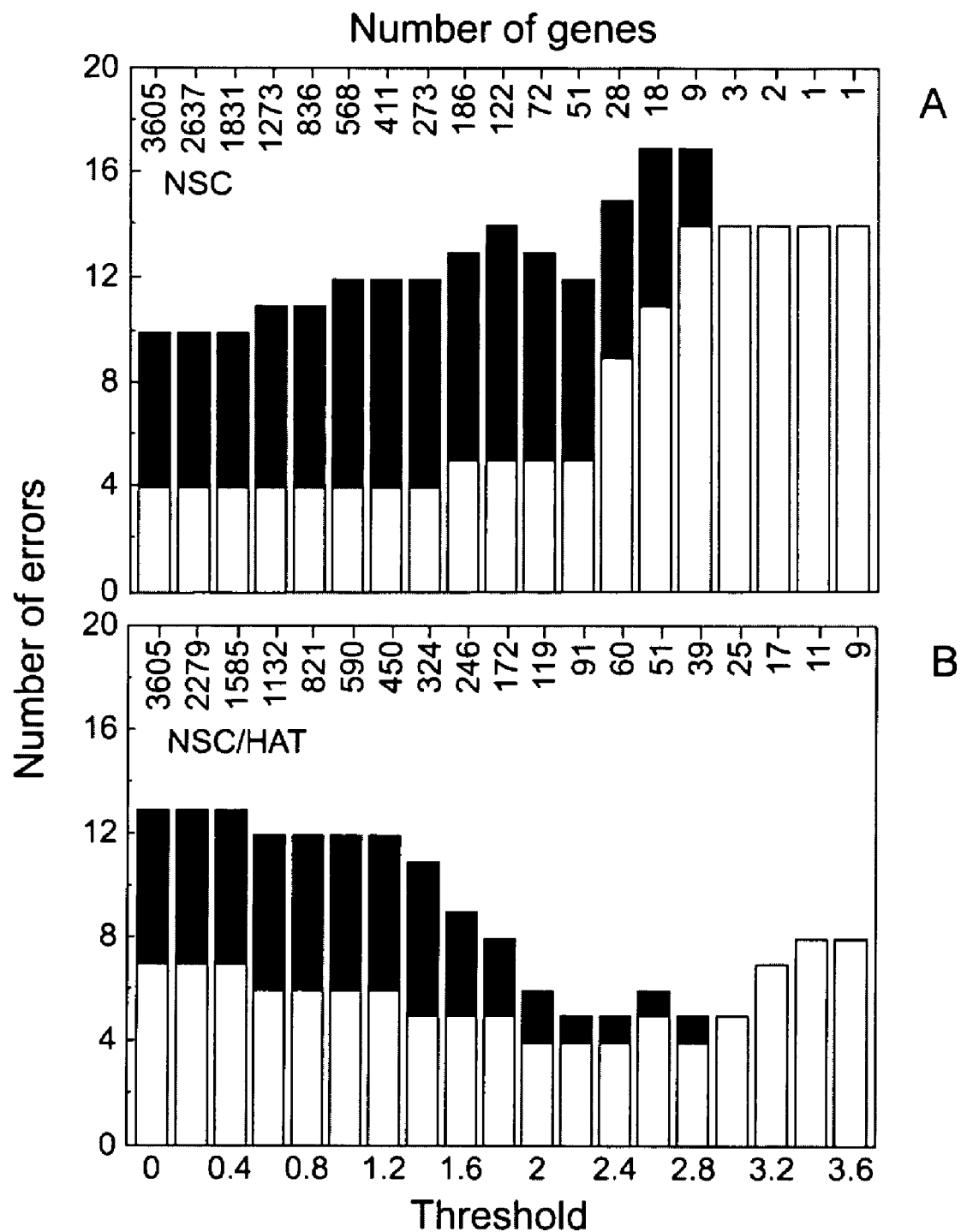
FIGS. 2A-2B. Effect of heterogeneity-associated transformation (HAT) on predictive power. The nearest shrunken centroid (NSC) classifier was applied to 1491 IR-responsive genes and 2114 UV-responsive genes identified by SAM. In the NSC method, the threshold parameter determines the number of genes used for prediction (shown above the bar graphs). The upper and lower panels show the number of errors with and without HAT, respectively. White bars indicate the number of false negatives, and black bars indicate the number of false positives.

Genes with heterogeneous transcriptional responses were successfully identified after transforming the data with HAT. FIG. 1 shows the effect of HAT on two predictive genes, cyclin B and 8-oxo-dGTPase. When x'(i) replaced x(i) for the set of 1491 IR-responsive genes and 2114 UV-responsive genes, NSC identified a subset of 24 genes that predicted radiation toxicity, with 5 false negatives and no false positives (FIG. 2). The low error rate occurred for a wide range of threshold values for the nearest shrunken centroid classifier. Thus, HAT enhanced the power of NSC, suggesting that the radiation sensitive patients constitute a heterogeneous group.

Prediction of radiation toxicity. Of the 24 predictive genes, 20 were IR-responsive, and 4 were UV-responsive. NSC/HAT used these responses to compute a probability of radiation toxicity for each subject in the 48-sample training set (FIG. 3, upper panel). The separation between the radiation sensitive patients and controls indicated a strong correlation between the responses of the 24 genes and radiation toxicity. This correlation was confirmed by 14-fold cross-validation, which predicted radiation toxicity in 9 of 14 patients, with no false positives among 43 controls, which included the 9 subjects previously used to identify the damage response genes, $p=2.2\times10^{-7}$ by Fisher's two-tailed exact test (FIG. 3, lower panel).

Figure 4:
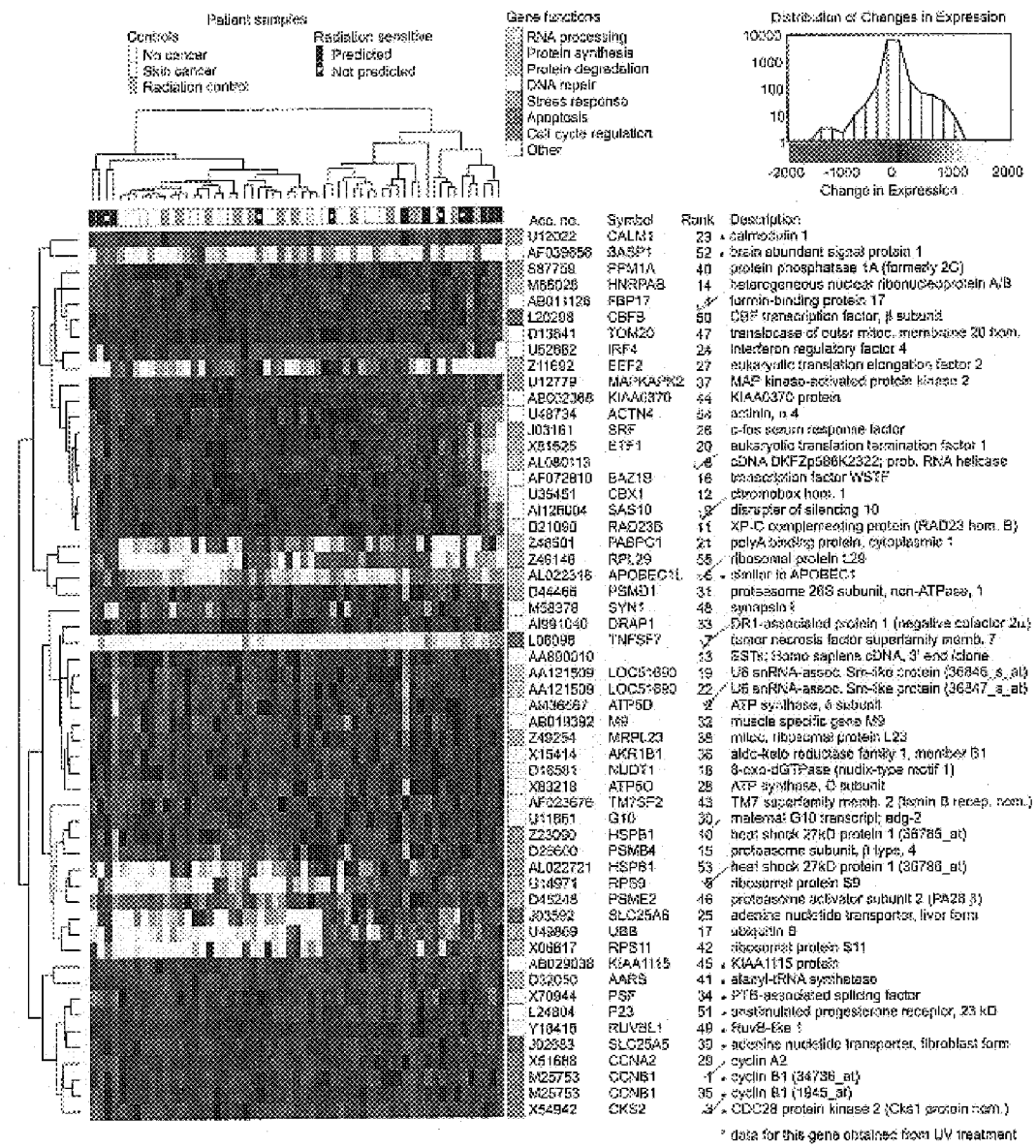

The genes identified during cross-validation were essentially the same as the genes identified from the full 48-sample training set. Among the 24 genes identified for each of the 14 cross-validation trials, 80% were among the 24 top-ranked genes from the 48-sample training set, and 99% were among the 52 top-ranked genes from that set (FIG. 4). To test the stability of the cross-validation protocol, we performed 10 new trials of 14-fold cross-validation by withholding different subsets of patients. All 10 trials successfully predicted toxicity in the same 9 of 14 patients with no false positives among the controls.

Delayed toxicity in the form of progressive damage after completion of treatment is a grave problem. Three patients (RadS6, RadS7, and RadS10) suffered grade 4 delayed toxicity, and all were predicted successfully (Table 4). Toxicity from non-genetic factors cannot be predicted by our approach. Of the 5 patients with radiation toxicity not predicted by NSC/HAT, at least 2 (RadS3 and RadS5) were at high risk for toxicity from non-genetic factors. Patient RadS3 suffered grade 3 mucositis from an experimental protocol that included high dose radiation plus tirapazamine, cisplatin, and 5-FU. Subsequent review of patients treated by this protocol revealed that 28 of 62 (45%) suffered mucositis of grade 3 or higher. Patient RadS5 had an arteriovenous malformation that was treated with stereotactic guidance of a single 18 Gy dose to a 1.8 $cm^3$ volume in the midbrain and pons. A statistical model indicates that the midbrain and pons region has the highest probability for permanent symptomatic injury, with a 40% to 45% probability for the dose and volume delivered to RadS5. To determine whether RadS3 and RadS5 had an effect on the results, we excluded them and repeated the analysis. Despite the decreased number of samples available for training, NSC/HAT successfully predicted toxicity in 9 of the remaining 12 cases, with no false positives among 43 controls.

Ruling out confounding variables. The enormous number of genes analyzed by microarrays offers great opportunity for discovery. However, transcriptional responses that appear to be predictive might instead be due to a confounding variable. Here, the confounding variable could be some other difference between the radiation sensitive patients and the control subjects. The subjects with no cancer or skin cancer were younger than the subjects with radiation toxicity. They were also free of cancers of the internal organs, which might be associated with an abnormal response to DNA damage. Furthermore, they were never treated with IR, and 5% to 10% might be at risk for toxicity. To address this problem, we omitted the 30 subjects with no cancer or skin cancer and analyzed the 27 radiation therapy patients. This restricted analysis was also successful despite the fewer samples available for training. A set of 13 genes yielded the same 5 false negatives reported above, with no false positives among the 13 controls. When tested on the 30 omitted subjects, these 13 genes predicted only 3 positives, consistent with the expected low risk for toxicity in the general population. The set of predictive genes was stable in the face of restricted analysis. Nine of the 13 genes were among the 24 top-ranked genes identified with the 48-sample training set, and 20 of the 24 predictive genes from the 48-sample training set were among the top 81 ranked genes in the restricted analysis.

Heterogeneity among the radiation sensitive patients. The 57 subjects and 52 top-ranked predictive genes identified by HAT/NSC were organized by hierarchical clustering (FIG. 4). The 52 genes were obtained from the 48-sample training set and included 40 IR-responsive genes and 12 UV-responsive genes. The radiation sensitive patients did not form a single cluster, suggesting that radiation toxicity arises from more than one type of underlying defect. Four radiation sensitive patients clustered loosely on the left side of the heat map. Cells from these patients had abnormal responses in many of the 52 genes, including the cluster of 9 UV-responsive genes at the bottom of the heat map. These patients may have a general defect in responding to DNA damage. Five radiation sensitive patients clustered on the right side of the heat map. These patients had a relatively normal response in the UV-response gene cluster, but had prominent defects in IR-response genes.

Genes with transcriptional responses that predict radiation toxicity. No single gene predicted radiation toxicity. Instead, the response of several genes provided a signature for toxicity. The 52 top-ranked predictive genes are involved in several different cellular processes (FIG. 4).

Four genes had roles in DNA repair. XPC-complementing protein (RAD23 homolog B) is involved in nucleotide excision repair. Its response to IR was abnormal in many radiation sensitive samples. The 8-oxo-dGTPase gene product (NUDT1) hydrolyzes 8-oxo-dGTP to 8-oxo-dGMP, which is then converted to the nucleoside, 8-oxo-dG, thus preventing misincorporation of 8-oxo-dGTP into DNA. Urinary 8-oxo-dG is a biomarker for oxidative DNA damage, and decreased levels correlated with acute radiosensitivity in breast cancer patients. These results may be explained by the abnormal IR-suppressed expression of 8-oxo-dGTPase we observed in several radiation sensitive patients (FIG. 1). IR-induced DNA double-strand breaks are repaired by homologous recombination (HR) or nonhomologous end-joining.

Human RuvB-like protein 1 (RUVBL1) is homologous to bacterial RuvB, a DNA helicase that catalyses branch migration of Holliday junctions during HR. RuvB-like proteins are also components of the yeast INO80 complex, which remodels chromatin, and confers resistance to DNA damaging agents. PTB-associated splicing factor (PSF) may be involved in HR by promoting DNA strand invasion. Interestingly, RUVBL1 and PSF responded abnormally to UV but not IR in many radiation sensitive patients. None of the 52 top-ranked predictive genes was involved in nonhomologous end-joining. However, this pathway does not respond to IR transcriptionally, but rather involves activation of a DNA-dependent protein kinase.

Five predictive genes are involved in the general stress response. Cells from radiation sensitive patients showed abnormal IR responses in genes encoding c-fos, MAP kinase-activated protein kinase 2 (MAPKAP2), heat shock protein 27 (HSPB1), which is a substrate of MAPKAP2 phosphorylation, and protein phosphatase 1A (PPM1A), which inhibits stress-activated protein kinase cascades. Abnormal UV responses were observed for calmodulin (CALM1).

Four predictive genes are involved in the ubiquitin/proteasome protein degradation pathway, which is induced by oxidative stress. Abnormal IR responses were observed for ubiquitin B (UBB), proteasome activator subunit (PSME2), and two subunits of the 26S proteasome, β subunit 4 (PSMB4) and the non-ATPase subunit 1 (PSMD1).

Three cell cycle genes responded abnormally to UV in some radiation sensitive patients: cyclin B1 (CCNB1), cyclin A2 (CCNA2), and CDC28 protein kinase 2 (CKS2), which negatively regulates CDK-cyclin complexes.

Apoptosis genes included tumor necrosis factor (TNFSF7), core binding factor (CBFB), and the mitochondrial adenine nucleotide transporter (ANT). ANT regulates mitochondrial membrane permeability during apoptosis. The fibroblast isoform of ANT (SLC25A6) responded abnormally to IR, and the liver isoform (SLC25A5) responded abnormally to UV in most radiation sensitive patients. Four predictive genes were involved in RNA processing, and the remaining 18 predictive genes were involved in a diverse set of pathways.

Many cases of radiation toxicity are associated with abnormal transcriptional responses to DNA damage. To identify a subset of highly predictive genes, we subjected the transcriptional responses to a heterogeneity-associated transformation (HAT). Classification by nearest shrunken centroids (NSC) with HAT predicted 9 of 14 cases of radiation toxicity with no false positives among 43 controls. Notably, the false positive rate was very low with a 95% confidence interval of 0% to 7%. Toxicity was successfully predicted in 64% of the radiation sensitive patients with a 95% confidence interval of 42% to 87% by the exact binomial distribution. Even the lower limit of this confidence interval suggests that a significant number of adverse radiation reactions are associated with abnormal transcriptional responses. Furthermore, 2 of the 5 patients not predicted by NSC/HAT were at high risk for radiation toxicity from non-genetic factors and may have been properly classified in terms of transcriptional responses.

These results are valid for several reasons. First, to guard against the identification of genes that later fail when tested on an independent set of samples, our results were subjected to cross-validation. We used 14-fold cross-validation, which is more robust than the commonly used "leave-one-out" approach. Second, we imposed the additional test of restricted analysis to rule out confounding variables; when we restricted the training set to the 27 radiation therapy patients, there was little effect on prediction error or on the identity of predictive genes. Third, we applied nearest centroids with HAT to the IR responses of all 12,625 probe sets on the microarray. On cross-validation, we successfully predicted 8 of 14 cases of radiation toxicity (RadS5, RadS7, and RadS9-14) with only 2 false positives (RadC8 and RadC9) among the 43 controls. Thus, our results were not an artifact of gene selection bias.

Finally, our protocol for predicting radiation toxicity used a plausible biological endpoint, the transcriptional response to DNA damage. Appropriately, 20 of the 24 top-ranked genes contributed IR responses, and only 4 genes contributed UV responses. When we attempted to predict radiation toxicity from the less plausible endpoint of basal gene expression, we obtained a low error rate after cross-validation. However, basal expression failed our additional test of restricting analysis to the radiation therapy patients; the prediction error rate increased significantly, and the set of predictive genes changed markedly, indicating the presence of confounding variables that affected basal gene expression.

The mechanisms of radiation toxicity are heterogeneous. Some radiation sensitive patients had abnormal transcriptional responses to both UV and IR, and others had abnormal responses only to IR. The abnormal responses involved genes from a diverse set of pathways with functions in DNA repair, response to stress, protein degradation, cell cycle regulation, apoptosis, and RNA processing. The genes with abnormal responses may not be mutated, but rather reflect an abnormality in some other gene. For example, abnormal responses in both UV and IR could arise from mutations affecting p53 or ATR. In patients with abnormal responses restricted primarily to IR, the underlying mutations could be in the ATM-dependent signaling pathway or a DNA double-strand break repair pathway. Radiation toxicity may also arise from the combined effect of polymorphisms in several genes.

It is evident that subject invention provides a convenient and effective way of determining whether a patient will be responsive to therapy. The subject methods will provide a number of benefits, including avoidance of delays in alternative treatments, elimination of exposure to adverse effects of therapeutic antibodies and reduction of unnecessary expense. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining the suitability of a patient for radiation therapy, the method comprising:
    predicting whether a subject will be susceptible to undesirable toxicity resulting from treatment with radiation therapy, said method comprising:
    (a) obtaining transcriptional expression profile for the response to radiation for a sample from said subject from a set of sequences comprising:
    Cyclin B, ATP synthase, CDC28, protein kinase 2, forming-binding protein 17, ribosomal protein 17, ribosomal protein S9, phorbolin-like protein MDS019, tumor necrosis factor superfamily member 7, RNA helicase disrupter of silencing 10, heat shock 27 kD protein 1
    (b) comparing said obtained expression profile to a reference expression profile from a cell known to have a susceptible phenotype for radiation toxicity to determine the probability that said patient is susceptible to undesirable radiation toxicity;
    wherein a patient that is predicted to have a high probability of undesirable radiation toxicity is less suitable for radiation therapy.

2. The method according to claim 1, wherein said expression profile further comprises expression data from RAD23 homolog B, chromobox homlog 1, heterogeneous nuclear ribonucleoprotein A/B, proteasome subnunit beta type 4, Bromodomain adjacent to zinc finger domain, ubiquitin, nudix-type motif 1, U6 snRNA-associated Sm-like protein, eukaryotic translation termination factor 1, poly(A)-binding protein cytoplasmic 1, U6 snRNA-associated Sm-like protein LSm7, calmodulin, interferon regulatory factor 4, solute carrier family 25 (mitochondrial carrier; adenine IR nucleotide translocator) member 6, serum response factor (c-fos serum response IR element-binding transcription factor), eukaryotic translation elongation factor 2, ATP synthase H+ transporting, mitochondrial F1 complex, O subunit (oligomycin sensitivity conferring protein), cyclin A2, maternal G10 transcript, proteasome (prosome, macropain) 26S subunit non-ATPase 1, muscle specific gene, DR1-associated protein 1 (negative cofactor 2 alpha) splicing factor proline/glutamine rich (polypyrimidine UV tract-binding protein-associated), Cyclin B1, aldo-keto reductase family 1 member B1 (aldose IR reductase), mitogen-activated protein kinase-activated protein kinase 2, mitochondrial ribosomal protein L23, solute carrier family 25 (mitochondrial carrier; adenine nucleotide translocator) member 5, protein phosphatase 1A (formerly 2C) magnesium-dependent alpha isoform, alanyl-tRNA synthetase, ribosomal protein S11, transmembrane 7 superfamily member 2, KIAA0370 protein, KIAA1115 protein, proteasome (prosome, macropain) activator subunit 2 (PA28 beta), translocase of outer mitochondrial membrane 20, (yeast) homolog, RuvB (*E coli* homolog)-like 1, core-binding factor, beta subunit.

3. The method according to claim 1, wherein said undesirable toxicity is at least a grade 2 toxicity.

4. A method of optimizing radiation therapy for a patient, the method comprising:
    (a) obtaining transcriptional expression profile for the response to radiation for a sample from said subject from a set of sequences comprising:
    Cyclin B, ATP synthase, CDC28, protein kinase 2, forming-binding protein 17, ribosomal protein 17, ribosomal protein S9, phorbolin-like protein MDS019, tumor necrosis factor superfamily member 7, RNA helicase disrupter of silencing 10, heat shock 27 kD protein 1; and
    (b) comparing said obtained expression profile to a reference expression profile from a cell known to have a susceptible phenotype for toxicity from the anti-proliferative therapy to determine the probability that said patient is susceptible to undesirable toxicity;
    wherein a dose of said anti-proliferative therapy is selected to minimize to undesirable toxicity, while providing for effective anti-proliferative activity.

5. A method of obtaining an expression profile for the transcriptional response to radiation, the method comprising:
    exposing a cell sample from an individual to radiation;
    extracting mRNA from said cell;
    quantitating the level of mRNA from a set of sequences comprising:
    Cyclin B, ATP synthase, CDC28, protein kinase 2, forming-binding protein 17, ribosomal protein 17, ribosomal protein S9, phorbolin-like protein MDS019, tumor necrosis factor superfamily member 7, RNA helicase disrupter of silencing 10, heat shock 27 kD protein 1; and
    comparing said level of mRNA to the level of said mRNA present in a cell sample from said individual not exposed to radiation, wherein said comparing step comprises a nearest shrunken centroid analysis step.

6. The method according to claim 5, wherein said exposing to radiation comprises exposes said cell to a dose of ionizing radiation of from about 2 to about 10 Gy.

7. The method according to claim 6, wherein said mRNA is extracted after at least about 2 and not more than about 24 hours following said exposure.

8. The method according to claim 6, further comprising exposing a cell sample from said individual to ultraviolet radiation at a dose of at least about 5 J/m$^2$ and not more than about 50 J/m$^2$.

9. The method according to claim 8, wherein said mRNA is extracted after at least about 4 and not more than about 72 hours following said exposure.

10. The method of claim 1, wherein the comparing step is performed with shrunken centroid analysis.

11. The method of claim 4, wherein said expression profile further comprises expression data from from RAD23 homolog B, chromobox homlog 1, heterogeneous nuclear ribonucleoprotein A/B, proteasome subnunit beta type 4, Bromodomain adjacent to zinc finger domain, ubiquitin, nudix-type motif 1, U6 snRNA-associated Sm-like protein, eukaryotic translation termination factor 1, poly(A)-binding protein cytoplasmic 1, U6 snRNA-associated Sm-like protein LSm7, calmodulin, interferon regulatory factor 4, solute carrier family 25 (mitochondrial carrier; adenine IR nucleotide translocator) member 6, serum response factor (c-fos serum response IR element-binding transcription factor), eukaryotic translation elongation factor 2, ATP synthase H+ transporting, mitochondrial F1 complex, O subunit (oligomycin sensitivity conferring protein), cyclin A2, maternal G10 transcript, proteasome (prosome, macropain) 26S subunit non-ATPase 1, muscle specific gene, DR1-associated protein 1 (negative cofactor 2 alpha) splicing factor proline/glutamine rich (polypyrimidine UV tract-binding protein-associated), Cyclin B1, aldo-keto reductase family 1member B1 (aldose IR reductase), mitogen-activated protein kinase-activated protein kinase 2, mitochondrial ribosomal protein L23, solute carrier family 25 (mitochondrial carrier; adenine nucleotide translocator) member 5, protein phosphatase 1A (formerly 2C) magnesium-dependent alpha isoform, alanyl-tRNA synthetase, ribosomal protein S11, transmembrane 7 superfamily member 2, KIAA0370 protein, KIAA1115 protein, proteasome (prosome, macropain) activator subunit 2 (PA28 beta), translocase of outer mitochondrial membrane 20, (yeast) homolog, RuvB (*E coli* homolog)-like 1, core-binding factor, beta subunit.

12. The method of claim 11, wherein the comparing step is performed with shrunken centroid analysis.

* * * * *

UNITED STATES PATENT AND TRADEMARK OFFICE
CERTIFICATE OF CORRECTION

| | | |
|---|---|---|
| PATENT NO. | : 7,465,542 B2 | Page 1 of 1 |
| APPLICATION NO. | : 10/686322 | |
| DATED | : December 16, 2008 | |
| INVENTOR(S) | : Chu et al. | |

It is certified that error appears in the above-identified patent and that said Letters Patent is hereby corrected as shown below:

Col. 1, line 4;
In the Specification, please insert:

-- FEDERALLY-SPONSORED RESEARCH OR DEVELOPMENT

This invention was made with Government support under contracts CA077302 and CA075675 awarded by the National Institutes of Health. The Government has certain rights in this invention. --

Signed and Sealed this
Ninth Day of August, 2011

David J. Kappos
*Director of the United States Patent and Trademark Office*